United States Patent
Williams et al.

(10) Patent No.: US 6,245,512 B1
(45) Date of Patent: Jun. 12, 2001

(54) PROMOTER FOR VEGF RECEPTOR

(75) Inventors: Lewis T. Williams, Tiburon, CA (US); Kaoru Morishita, Tokyo (JP)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/263,914

(22) Filed: Mar. 5, 1999

Related U.S. Application Data

(62) Division of application No. 08/556,424, filed on Nov. 9, 1995, now Pat. No. 5,916,763.

(51) Int. Cl.$^7$ .............................. C12Q 1/68; C07H 21/04
(52) U.S. Cl. ........................ 435/6; 536/23.5; 435/320.1; 435/361; 435/7.1; 530/350
(58) Field of Search .......................... 530/350; 536/23.5; 435/320.1, 361, 6, 7.1

(56) References Cited

FOREIGN PATENT DOCUMENTS 7-289263    11/1995  (JP) .

OTHER PUBLICATIONS

Patterson, C., "Cloning and Functional Analysis of the Promoter for KDR/flk–1, a Receptor for Vascular Endothelial Growth Factor", The Journal of Biological Chemistry, vol. 270, No. 39, Sep. 1995, pp. 23111–23118.

Database on MPSRCH, n–geneseq24, No. Q74275, Kendall et al., "Vascular endothelial cell growth factor inhibitors–bind growth factor with high affinity but without signal transduction", Sep. 29, 1994.

B. Terman, et al., "Identification of the KDR Tyrosine Kinase as a Receptor for Vascular Endothelial Cell Growth Factor," Biochemical and Biophysical Research Communications, 187, (3): 1579–1576, (1992).

M. Shibuya et al., "Nucleotide Sequence and Expression of a Novel Human Receptor–type Tyrosine Kinase Gene (flt) Closely Related to the fms Family," Oncogene, 5 519–524 (1990).

C. De Vries, "The fms–Like Tyrosine Kinase, A Receptor for Vascular Endothelial Growth Factor," Science, 255, 989–991, (1992).

F. Galland et al., "Chromosomal Localization of FLT4, A Novel Receptor–Type Tyrosine Kinase Gene," Genomics, 13, 475–478, (1992).

K. Peters, et al., "Vascular Endothelial Growth Factor Receptor Expression During Embryogenesis and Tissue Repair Suggests A Role in Endothelial Differentiation and Blood Vessel Growth," Proc. Natl. Acad. Sci. USA, 90, 8915–8919, (1993).

K. Pajusola, et al., "FLT4 Receptor Tyrosine Kinase Contains Seven Immunoglobulin–Like Loops and is Expressed in Multiple Human tissues and Cell Lines," Cancer Research, 52 5738–5743, (1992).

J. Korhonen et al., "Endothelial–Specific Gene Expression Directed by the tie Gene Promoter In Vivo," Blood, 86 (5), 1828–1835, (1995).

Thorsten M. Schlaeger et al., "Vascular Endothelial Cell Lineage–Specific Promoter in Transgenic Mice," Development, 121., 1089–1098 (1995).

R. Kendall, et al., "Inhibitor of Vascular endothelial Cell Growth Factor," PCT WO 94/21679, (Sep. 29, 1994).

"FLK–1 is a Receptor for Vascular Endothelial Growth Factor,": PCT WO 94/11499, (May 26, 1994).

"Identification of a Novel Human Receptor Tyrosine Kinase Gene," PCT WO 92/14748, (Sep. 3, 1992).

Galland, et al., "The FLT4 gene encoded a transmembrane tyrosine kinase related to the vascular endothelial growth factor receptor," Oncogene, 8 (5) :1233–1240, May 1993.

Ikeda, et al., "Characterization of the Promotor Region for flt–1 Tyrosine Kinase Gene, A Receptor for Vascular Endothelial Growth Factor," Growth Factors, 13 : 151–162 (1996).

Morishita, et al., "A Novel Promoter for Vascular Endothelial Growth Factor Receptor (flt–1) That Confers Endothelial–specific Gene Expression,"Journal of Biological Chemistry, 270 (46):27948–27953, Nov. 17, 1995.

Pajusola, et al., "Two human FLT4 receptor tyrosine kinase isoforms with distinct carboxy terminal tails are produced by alternative processing of primary transcripts," Oncogene, 8:2931–2937 (1993).

Ronicke, et al., "Characterization of the Endothelium–Specific Murine Vascular Endothelial Growth Factor Receptor–2 (Flk–1) Promotor," Circulation Research, 79(2) : 277–285, Aug. 1996.

Primary Examiner—Lorraine Spector
Assistant Examiner—Eileen B. O'Hara
(74) Attorney, Agent, or Firm—Townsend & Townsend & Crew LLP

(57) ABSTRACT

This invention provides nucleic acid sequences for a VEGF receptor promoter, particularly for the Flt-1 promoter, expression vectors and recombinant host cells containing this promoter. It also provides methods for screening for drugs that regulate the transcriptional activity of the VEGF receptor promoter. Methods for endothelial-specific gene expression and treatment of disease, particularly by inhibiting angioigenesis, using novel gene constructs containing the VEGF receptor promoter are also provided. Transgenic animals having heterologous genes linked to the VEGF receptor promoter are also provided.

13 Claims, 8 Drawing Sheets

FIG. 2A

```
-1195   GTGGCAACTT TGGGTTACCC AACCTTCCTA GGCGGGGAGG TAGTCCAGTC
-1145   CTTCAGGAAG AGTCTCTGGC TCCGTTCAAG AGCCATCACA GTCCCTTGTA
-1095   TTACATCCCT CTGACGGGTT CCAATAGGAC TATTTTTCAA ATCTGCGGTA
-1045   TTTACAGAGA CAAGACTGGG CTGCTCCGTG CAGCCAGGAC GACTTCAGCC
-995    TTTGAGGTAA TGGAGACATA ATTGAGGAAC AACGTGGAAT TAGTGTCATA
-945    GCAAATGATC TAGGGCCTCA AGTTAATTTC AGCCGGTTGT GGTCAGAGTC
-895    ACTCATCTTG AGTAGCAAGC TGCCACCAGA AAGATTTCTT TTTCGAGCAT
-845    TTAGGGAATA AAGTTCAAGT GCCCTGCGCT TCCAAGTTGC AGGAGCAGTT
-795    TCACGCCTCA GCTTTTTAAA GGTATCATAA TGTTATTCCT TGTTTTGCTT
-745    CTAGGAAGCA GAAGACTGAG GAAATGACTT GGGCGGGTGC ATCAATGCGG
-695    CCGAAAAAGA CACGGACACG CTCCCCTGGG ACCTGAGCTG GTTCGCAGTC
-645    TTCCCAAAGG TGCCAAGCAA GCGTCAGTTC CCCTCAGGCG CTCCAGGTTC
-595    AGTGCCTTGT GCCGAGGGTC TCCGGTGCCT TCCTAGACTT CTCGGGACAG
-545    TCTGAAGGGG TCAGGAGCGG CGGGACAGCG CGGGAAGAGC AGGCAAGGGG
-495    AGACAGCCGG ACTGCGCCTC AGTCCTCCGT GCCAAGAACA CCGTCGCGGA
-445    GGCGCGGCCA GCTTCCCTTG GATCGGACTT TCCGCCCCTA GGGCCAGGCG
-395    GCGGAGCTTC AGCCTTGTCC CTTCCCCAGT TTCGGGCGGC CCCCAGAGCT
-345    GAGTAAGCCG GGTGGAGGGA GTCTGCAAGG ATTTCCTGAG CGCGATGGGC
-295    AGGAGGAGGG GCAAGGGCAA GAGGGCGCGG AGCAAAGACC CTGAACCTGC
-245    CGGGGCCGCG CTCCCGGGCC CGCGTCGCCA GCACCTCCCC ACGCGCGCTC
-195    GGCCCCGGGC CACCCGCCCT CGTCGGCCCC CGCCCCTCTC CGTAGCCGCA
-145    GGGAAGCGAG CCTGGGAGGA AGAAGAGGGT AGGTGGGGAG GCGGATGAGG
            ets              ets -95     GGTGGGGGAC CCCTTGACGT CACCAGAAGG AGGTGCCGGG GTAGGAAGTG
                    CAEB/ATF                                 ets -45     GGCTGGGGAA AGGTTATAAA TCGCCCCCGC CCTCGGCTGC TCTTCATCGA
           ets      TATA box
+6      GGTCCGCGGG AGGCTCGGAG CGCGCCAGGC GGACACTCCT CTCGGCTCCT +56     CCCCGGCAGC GGCGGCGGCT CGGAGCGGGC TCCGGGGCTC GGGTGCAGCG
                             Oligo-F
+106    GCCAGCGGGC GCCTGGCGGC GAGGATTACC CGGGGAAGTG GTTGTCTCCT

+156    GGCTGGAGCC GCGAGACGGG CGCTCAGGGC GCGGGGCCGG CGGCGGCGAA
```

FIG. 2B

+206 CGAGAGGACG GACTCTGGCG GCCGGGTCTT TGGCCGCGGG GAGCGCGGGC
                                                     ↳▶ Intron 1
+256 ACCGGGCGAG CAGGCCGCGT CGCGCTCACC ATGGTCAGCT ACTGGGACAC
+306 CGGGGTCCTG CTGTGCGCGC TGCTCAGCTG TCTGCTTCTC ACAGGTGAGG
+356 CGCGGCTGGG GGCCGGGGCC TGAGGCGGGC TGCGATGGGG CGGCCGGAGG
+406 GCAGAGCCTC CGAGGCCAGG GCGGGGTGCA CGCGGGGAGA CGAGGCTGTA
            Transcription arrest site
+456 GCCCGGAGAA GCTGGCTACG GCGAGAACCT GGGACACTAG TTGCAGCGGG
+506 CACGCTTGGG GCCGCTGCGC CCTTTCTCCG AGGGAGCGCC TCGAG

FIG. 8

```
                        +408                    +432
flt-1 intron            AGAGCCTCCGAGGCCAGGGCGGGGT
                        ** * ***** *******  **
ADA intron 1            AGGGGCTCCGTTGCCAGGGTTCTGT
                        +133                    +157
```

PROMOTER FOR VEGF RECEPTOR

This invention was made with Government support under Grant No. HL 43821, awarded by the National Institutes of Health. The Government has certain rights in this invention.

The present application is a Rule 60 Divisional Application of and claims the benefit of U.S. Pat. No. 5,916,763, which issued from U.S. patent application Ser. No. 08/556,424, filed on Nov. 9, 1995, which is incorporated by reference in its entirety for all purposes.

BACKGROUND OF THE INVENTION

1. Field of the Invention

This invention relates to a novel promoter for tissue specific gene expression and uses thereof. More particularly, this invention relates to nucleic acid sequences containing a functional promoter for the VEGF receptor, Flt-1 (fms-like receptor tyrosine kinase) that correspond in structure and/or properties to the native genomic form of this promoter, the use of such nucleic acid sequences in screening for drugs that affect the VEGF/Flt-1 regulatory pathway, the use of such nucleic acid sequences in endothelial specific gene expression and other therapeutic and diagnostic applications.

2. Background

The establishment of a vascular supply is a critical requirement for the cellular inflow of nutrients, outflow of waste products and gas exchange in most tissues and organs. Two separate processes for such blood vessel development and differentiation have been identified. One process, termed "vasculogenesis" takes place in the embryo and consists of the in situ differentiation of mesenchymal cells into hemoangioblasts which are the precursors of both endothelial cells and blood cells. The other process, termed "angiogenesis" is the formation of new blood vessels by sprouting from a preexisting endothelium. This process is required not only for the further development of the embryonic vasculature, but also for a wide variety of post natal processes such as wound healing and tissue and organ regeneration. In addition, angiogenesis has been identified as a critical requirement for solid tumor growth and uncontrolled blood cell proliferation is an important pathogenic component in a variety of other disorders such as rheumatoid arthritis, atherosclerosis, diabetes mellitus, retinopathies, psoriasis and retrolental fibroplasia (all of which are characterized by excessive angiogenesis). Therefore, there is much interest in identifying angiogenesis factors and their receptors, identifying their mechanisms of action with the goals of agonizing or antagonizing their activity and using their activity as a prognostic predictor of disease state.

Recently, vascular endothelial growth factor (VEGF)/vascular permeability factor (VPF) has been identified as a prime regulator of normal and pathological angiogenesis. VEGF is a secreted growth factor which has the following properties: (1) it is a remarkably specific mitogen for endothelial cells; (2) it is angiogenic in vivo and induces vascular permeability; (3) expression of VEGF and its receptors correlates with vasculogenesis and angiogenesis during embryonic development; and (4) VEGF is expressed in tumor cells, whereas the VEGF receptor is expressed exclusively in adjacent small blood vessels. VEGF plays a crucial role for the vascularization of a wide range of tumors including breast cancers, ovarian tumors, brain tumors, kidney and bladder carcinomas, adenocarcinomas and malignant gliomas. Tumors produce ample amounts of VEGF, which stimulates the proliferation and migration of endothelial cells (ECs), thereby inducing tumor vascularization by a paracrine mechanism.

The angiogenic effect of VEGF is mediated by its binding to high affinity cell surface VEGF receptors. Recently, three such high affinity receptors, Flt-1 (fms-like tyrosine kinase), Flk-1(fetal liver kinase-1; mouse homologue of kinase insert domain-containing receptor (KDR)) and Flt-4, have been cloned and identified. These receptors are members of the type III subclass of the family of tyrosine kinases. The type III subclass is characterized by proteins containing seven immunoglobulin-like domains, a single transmembrane region, and a kinase insert sequence. Of these, Flt-1 and Flk-1 are highly expressed by the endothelial cells in tumor blood vessels. In particular, high levels of Flt-1 expression are detected during periods of endothelial cell differentiation and neovascularization during wound healing and embryonic vascular development. Since endothelial cell differentiation drives tumor angiogenesis by promoting vascular permeability of the developing tumor blood vessels, inhibition of the production and activity of the VEGF/Flt-1 ligand/receptor system is a significant target for antiangiogenic anticancer strategies using anti-sense techniques, specific antibodies and specific inhibitors of VEGF/Flt-1 interactions.

Similarly, Flt-1 has been shown to be essential for the organization of the embryonic vasculature. Furthermore, Flt-1 is significantly up-regulated in a variety of disease states such as papillary dermal edemas, hemangioblastomas, cytokine-induced cell proliferation, CNS tumors and malignant gliomas. In comparison, there was little or no receptor expression in normal brain vasculature. Northern blot and in situ hybridization analysis showed significant Flt-1 mRNA transcription in capillary hemangioblastoma cells compared to normal brain cells. Therefore, it is believed that Flt-1 is induced during tumor progression and that the VEGF/Flt-1 signalling pathway plays a significant role in stimulating tumor angiogenesis, a requirement for solid tumor growth.

Though Flt-1 expression is greatly enhanced in diseased tissue such as solid tumors, little is known about the regulation of its expression. In addition, although as described earlier, Flt-1 expression is localized in endothelial cells, particularly in the vascular endothelium, little is known about its molecular regulation in the endothelium. Whereas the genomic DNA sequence of a related receptor tyrosine kinase containing two immunoglobulin-like domains, Tie, and its promoter region has been reported, the sequence of the promoter region of Flt-1 and other receptor tyrosine kinases of the type III subclass are not known. Knowing the promoter region of Flt-1 and other promoters of the type III subclass would enable the regulation of Flt-1 and the other type III subclass receptor tyrosine kinases. Regulation of Flt-1 expression would provide methods of inhibiting diseases associated with excessive angiogenesis of the vascular endothelium and promoting the processes of organ regeneration such as wound healing and the like. More generally, endothelial cells and the promoter elements controlling endothelial-specific gene expression are useful in the study of and therapy for diseases involving the vascular system, e.g., hemostasis, wound healing, atherosclerosis, hypertension, diabetic retinopathy, rheumatoid arthritis, blood cell trafficking, inflammatory conditions and tumor angiogenesis. Endothelial cells are in direct contact with blood and are therefore optimally situated for production of and secretion of desired proteins into the bloodstream or to neighboring cells. Expression systems where a gene is attached to an appropriate regulatory element targeted specifically to endothelial cells would allow for specific delivery of therapeutic agents to the endothelium. The novel promoters, nucleic acid sequences and screening assays provided by this invention fulfill these and other needs.

3. Summary of Related Art

Identification of the KDR Tyrosine Kinase as a Receptor for Vascular Endothelial Cell Growth Factor; B. Terman, M Dougher-Vermazen, M. Carrion, D. Dimitrov, D. Armellino, D Gospodarowicz, and P. Böhlen; *Biochemical and Biophysical research Communications*, V.187, No.3, 1579–1586, (1992); discloses cDNA and predicted amino acid sequence for KDR.

Nucleotide sequence and expression of a Novel Human Receptor-type Tyrosine kinase gene (flt) closely related to the fms family; M. Shibuya et al., *Oncogene*, 5, 519–524 (1990); discloses cDNA sequence of human Flt-1 gene.

The fms-Like Tyrosine Kinase, a Receptor for Vascular Endothelial Growth Factor; C. de Vries, J. Escobedo, H. Ueno, K. Houck, N. Ferrara, L. Williams; *Science*, 255, 989–991, (1992); describes cloning of human Flt-1.

Chromosomal Localization of FLT4, a Novel Receptor-Type Tyrosine Kinase Gene; F. Galland et al., *Genomics*, 13, 475–478, (1992); discloses the isolation, partial CDNA sequence and chromosomal localization of human Flt-4 and its deduced amino acid sequence.

Vascular endothelial growth factor receptor expression during embryogenesis and tissue repair suggests a role in endothelial differentiation and blood vessel growth; K. Peters, C. De Vries, L. Williams; *Proc. Natl. Acad. Sci. USA*, 90, 8915–8919, (1993); discloses that Flt-1 expression was localized in the endothelium.

FLT4 Receptor Tyrosine Kinase Contains seven Immunoglobulin-like Loops and Is Expressed in Multiple Human Tissues and Cell Lines; K. Pajusola, O. Aprelikova, J. Korhonen, A. Kaipainen, L. Pertovaara, R. Alitalo, K. Alitalo; *Cancer Research*, 52, 5738–5743, (1992); discloses cDNA sequence for Flt-4.

Endothelial-Specific Gene Expression Directed by the tie Gene Promoter In Vivo; J. Korhonen et al., *Blood*, V.86, No.5, 1828–1835, (1995); discloses the human and mouse Tie gene promoter sequences.

Vascular Endothelial Cell lineage-specific Promoter in Transgenic Mice; Thorsten M. Schlaeger et al., *Development*, 121, 1089–1098 (1995); studied function of Tie-2 gene promoter in transgenic mice and embryonic stem cells.

Inhibitor of Vascular Endothelial Cell Growth Factor; R. Kendall, K. Thomas; PCT WO 94/21679, published Sep. 29, 1994; discloses soluble mutants of Flt-1 which bind VEGF with high affinity but do not result in signal transduction.

FLK-1 is a Receptor for Vascular Endothelial Growth Factor; PCT WO 94/11499, published May 26, 1994; discloses cloning of mouse Flk-1, uses of expressed Flk-1 to screen for drugs and inhibition of tumor growth using mouse cells encoding a transdominant-negative truncated Flk-1 mutant receptor.

Identification of a Novel Human Receptor Tyrosine Kinase Gene; PCT WO 92/14748, published Sep. 3, 1992; discloses the CDNA sequence of human KDR.

SUMMARY OF THE INVENTION

This invention relates to a substantially purified nucleic acid molecule comprising a VEGF receptor promoter region, such as the promoters of the high affinity receptor tyrosine kinase subclass type III family and in particular the Flt-1 promoter.

This invention also relates to a nucleic acid molecule having a sequence selected from the group consisting of:
(a) a nucleic acid sequence substantially homologous to that of FIG. 2 (SEQ ID NO:1), or a fragment thereof, exhibiting promoter activity;
(b) a nucleic acid sequence substantially complementary to the nucleic acid sequence of (a) or a fragment thereof;
(c) a nucleic acid sequence that hybridizes to the nucleic acid sequences of (a) or (b) or fragments thereof; and
(d) a nucleic acid identical to any of the sequences of (a), (b) or (c), with the proviso that any T may have been replaced by U.

The invention also relates to expression vectors comprising the aforementioned nucleic acid sequences and host cells transformed with these expression vectors.

The invention also relates to methods for detecting test agents which modulate transcription of the VEGF receptor promoters described above comprising contacting a host cell transformed with an expression vector comprising the VEGF receptor promoter DNA sequence operably linked to a reporter gene with the test agent and comparing the level of transcription produced by the test agent to the level of transcription produced in its absence.

One aspect of the invention provides methods of screening for test compounds that regulate the activity of the VEGF receptor promoter by:
(a) contacting a host cell in which the VEGF receptor promoter disclosed herein is operably linked to a reporter gene with a test medium containing the test compound under conditions which allow for expression of the reporter gene;
(b) measuring the expression of the reporter gene in the presence of the test medium;
(c) contacting the host with a control medium which does not contain the test compound but is otherwise identical to the test medium in (a), under conditions identical to those used in (a);
(d) measuring the expression of reporter gene in the presence of the control medium; and
(e) relating the difference in expression between (b) and (d) to the ability of the test compound to regulate the activity of the VEGF receptor promoter.

Another aspect of this invention provides methods of measuring the ability of a test compound to modulate VEGF receptor transcription by:
(a) contacting a host cell in which the VEGF receptor promoter disclosed herein is operably linked to a reporter gene with an inducer of VEGF receptor promoter activity under conditions which allow for expression of the reporter gene;
(b) measuring the expression of the reporter gene in the absence of the test compound;
(c) exposing the host cells to the test compound either prior to, simultaneous with, or after contacting, the host cells with the inducer;
(d) measuring the expression of the reporter gene in the presence of the test compound; and
(e) relating the difference in expression between (b) and (d) to the ability of the test compound to modulate the transcription of the VEGF receptor.

The invention also relates to methods of modulating angiogenesis or thrombogenesis in a mammal comprising introducing into endothelial cells a vector comprising the nucleic acid sequence encoding a VEGF receptor promoter operably linked to a nucleic acid sequence encoding a protein, polypeptide, hormone, ribozyme or antisense RNA, which decrease vascular permeability and/or have antimitogenic activity or inhibit thrombogenesis and expressing the nucleic acid sequence.

The invention also relates to transgenic or chimeric animals whose cells express a heterologous gene under the transcriptional control of a VEGF receptor promoter, particularly the Flt-1 promoter.

BRIEF DESCRIPTION OF THE DRAWINGS

FIG. 2 Nucleotide sequence (SEQ ID NO:1) of the 5' flanking region, exon 1, and a 5' portion of intron 1 of the Flt-1 gene. Position −1195 of FIG. 2 corresponds to residue 1 of SEQ ID NO:1 and position +550 of FIG. 2 corresponds to residue 1745 of SEQ ID NO:1. The numbering system used in the text is that shown in FIG. 2. The transcription initiation site identified by primer extension and S1 mapping is indicated by an asterisk and designated as +1 (FIG. 3). The consensus sequence of a TATA box, the putative binding sites for CREB/ATF (cAMP response element binding protein/activating transcription factor) and Ets (E26 transformation specific sequence), and the putative transcription arrest site are underlined. A unique separated palindromic sequence is boxed. The nucleotide sequence of the synthetic oligonucleotide oligo-F used for primer extension is also underlined. The 5' end of intron 1 is indicated by an arrow.

FIG. 8. Comparison between the sequence surrounding the transcription arrest site in the first intron (SEQ ID NO: 2) of the adenosine deaminase gene and the homologous region in the first intron of flt-1 (residues 1603 to 1627 of SEQ ID NO: 1). Asterisks indicate identical bases. The core sequence of the transcription arrest site is boxed. The underlined bases have been shown to be important for full transcription arrest activity by point mutational analysis.

DETAILED DESCRIPTION OF THE INVENTION

Figure 1:
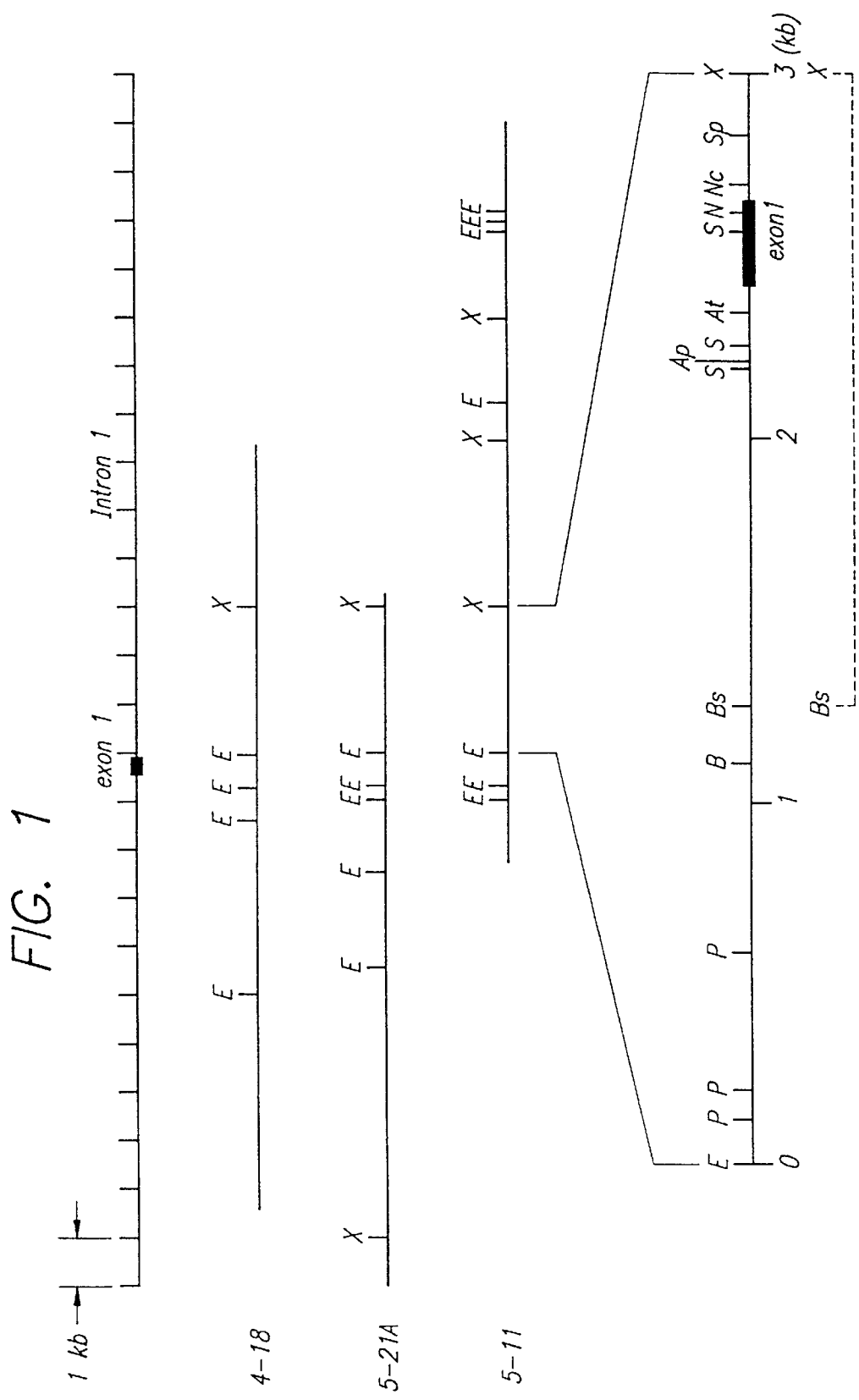
FIG. 1 Structure and restriction map of the Flt-1 genomic clones containing a 5' flanking region, exon 1, and a 5' portion of intron 1. Three clones contained overlapping genomic segments. Solid boxes indicate the position of exon 1. The 3-kb EcoRI/XhoI fragments from all three clones were subcloned into pBluescript and restriction sites were determined. Restriction patterns of the three fragments were identical. The nucleotide sequence of the 5' flanking region of Flt-1 between positions −1195 (BstXI) and +550 (XhoI) indicated by dotted line was determined by the Sanger method. Restriction sites for enzymes are indicated as follows: ApaI, Ap; AatII, At; B, BamHI; Bs, BstXI; E, EcoRI; N. NaeI; Nc, NcoI; P, PstI; S, SmaI; Sp, SpeI; X, XhoI.

This invention relates to novel promoters for the VEGF receptor, nucleic acid constructs comprising such promoters operatively linked to genes encoding a gene product, such as a protein, polypeptide, hormone, ribozyme, or antisense RNA, recombinant cells comprising such nucleic acid constructs, screening for therapeutic drugs using such cells and endothelial tissue-specific gene expression using these novel promoter sequences.

Before describing the invention in greater detail the following definitions are set forth to illustrate and define the meaning and scope of the terms used to describe the invention herein.

The term "receptor tyrosine kinase subclass type III" refers to the subfamily of receptor tyrosine kinases characterized by a high affinity binding site for VEGF (vascular endothelial growth factor) and containing seven immunoglobulin-like domains, a single transmembrane region, and a kinase insert sequence. These receptors are exemplified by Flt-1, Flt-4 and Flk-1/KDR.

The term "nucleic acid molecule" is meant to include DNA, RNA and mixed DNA-RNA sequences. In addition to the typically found A, T, U, G and C residues, a nucleic acid molecule may also include related residues such as, for example, inosine (I).

The term "promoter region" refers to a DNA sequence that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, calcium or cAMP responsive sites, and any other sequences of nucleotides known to one of skill in the art to act directly or indirectly to regulate the amount of transcription from the promoter.

The term "promoter activity" refers to the extent of transcription of a gene that is operably linked to the promoter whose promoter activity is being measured. The promoter activity may be measured directly by measuring the amount of RNA transcript produced, for example by Northern blot or indirectly by measuring the product coded for by the RNA transcript, such as when a reporter gene is linked to the promoter.

The term "substantially purified" refers to a nucleic acid sequence, polypeptide, protein or other compound which is essentially free, i.e. is more than about 50% free of, preferably more than about 70% free of, more preferably more than about 90% free of, the polynucleotides, proteins, polypeptides and other molecules that the nucleic acid, polypeptide, protein or other compound is naturally associated with.

The term "operably linked" refers to linkage of a DNA segment to another DNA segment in such a way as to allow the segments to function in their intended manners. A DNA sequence encoding a gene product is operably linked to a regulatory sequence when it is ligated to the regulatory sequence, such as, for example, promoters, enhancers and silencers, in a manner which allows modulation of transcription of the DNA sequence, indirectly or indirectly. For example, a DNA sequence is operably linked to a promoter when it is ligated to the promoter downstream with respect to the transcription initiation site of the promoter, in the correct reading frame with respect to the transcription initiation site and allows transcription elongation to proceed through the DNA sequence. An enhancer or silencer is operably linked to a DNA sequence coding for a gene product when it is ligated to the DNA sequence in such a manner as to increase or decrease respectively the transcription of the DNA sequence. Enhancers and silencers may be located upstream, downstream or embedded within the coding regions of the DNA sequence. A DNA for a signal sequence is operably linked to DNA coding for a polypeptide if it is expressed as a preprotein that participates in the secretion of the polypeptide. Linkage of DNA sequences to regulatory sequences is typically accomplished by ligation at suitable restriction sites or adapters or linkers inserted in lieu thereof using restriction endonucleases known to one of skill in the art.

The term "transcriptional regulator" refers to a biochemical element that acts to prevent or inhibit the transcription of a promoter-driven DNA sequence under certain environmental conditions (e.g., a repressor or nuclear inhibitory protein), or to permit or stimulate the transcription of the promoter-driven DNA sequence under certain environmental conditions (e.g., an inducer or an enhancer).

The term "induction" refers to an increase in gene transcription or expression brought about by a transcriptional inducer, relative to some basal level of transcription.

The term "repression" refers to a decrease in gene transcription or expression brought about by a transcriptional repressor, relative to some basal level of transcription.

The term "heterologous DNA" or "heterologous RNA" refers to DNA or RNA that does not occur naturally as part of the genome or DNA or RNA sequence in which it is present, or that is found in a cell or location or locations in the genome or DNA or RNA sequence that differs from that which it is in found in nature. Heterologous DNA and RNA is not endogenous to the cell into which it is introduced, but has been obtained from another cell or synthetically or recombinantly produced. Generally, though not necessarily, such DNA encodes RNA and proteins that are not normally produced by the cell in which the DNA is transcribed or expressed. similarly exogenous RNA encodes for proteins not normally expressed in the cell in which the exogenous RNA is present. Heterologous DNA or RNA may also referred to as foreign DNA or RNA. Any DNA or RNA that one of skill in the art would recognize as heterologous or foreign to the cell in which it is expressed is herein encompassed by the term heterologous DNA or heterologous RNA. Examples of heterologous DNA include, but are not limited to, DNA that encodes proteins, polypeptides, receptors, reporter genes, transcriptional and translational regulatory sequences, selectable or traceable marker proteins, such as a protein that confers drug resistance, RNA including mRNA and antisense RNA and ribozymes.

A "reporter gene" is a DNA molecule that expresses a detectable gene product, which may be RNA or protein. The detection may be accomplished by any method known to one of skill in the art. For example, detection of mRNA expression may be accomplished by using Northern blots and detection of protein may be accomplished by staining with antibodies specific to the protein. Preferred reporter genes are those that are readily detectable. A reporter gene may be operably linked in a DNA construct with a regulatory DNA sequence such that detection of the reporter gene product provides a measure of the transcriptional activity of the regulatory sequence. Examples of reporter genes include, but are not limited to, those coding for chloramphenicol acetyl transferase (CAT), luciferase, $\beta$-galactosidase and alkaline phosphatase.

The term "polynucleotide" as used herein refers to a polymeric form of nucleotides of any length, either ribonucleotides or deoxyribonucleotides. This term refers only to the primary structure of the molecule. Thus, this term includes double and single stranded DNA, triplex DNA, as well as double and single stranded RNA. It also includes modified, for example, by methylation and/or by capping, and unmodified forms of the polynucleotide.

The term "recombinant polynucleotide" as used herein refers to a polynucleotide of genomic, cDNA, semisynthetic or synthetic origin which, by virtue of its origin or manipulation: (1) is not associated with all or a portion of the polynucleotide with which it is associated in nature and/or (2) is linked to a polynucleotide other than that to which it is linked in nature.

The term "cDNA" or complementary DNA refers to single stranded or double stranded DNA sequences obtained by reverse transcription of messenger RNA isolated from a donor cell. For example, treatment of messenger RNA with a reverse transcriptase such as AMV reverse transcriptase or M-MuLV reverse transcriptase in the presence of an oligonucleotide primer will furnish an RNA-DNA duplex which can be treated with RNase H, DNA polymerase and DNA ligase to generate double stranded cDNA. If desired, the double stranded cDNA can be denatured by conventional techniques such as shearing to generate single stranded cDNA.

An "expression vector" is any genetic element, e.g., a plasmid, a chromosome, a virus, behaving either as an autonomous unit of polynucleotide replication within a cell (i.e. capable of replication under its own control) or being rendered capable of replication by insertion into a host cell chromosome, having attached to it another polynucleotide segment, so as to bring about the replication and/or expression of the attached segment. Suitable vectors include, but are not limited to, plasmids, bacteriophages and cosmids. Vectors may contain polynucleotide sequences which are necessary to effect ligation or insertion of the vector into a desired host cell and to effect the expression of the attached segment. Such sequences differ depending on the host organism; they include promoter sequences, such as the novel Flt-1 promoters of the present invention, to effect transcription, enhancer sequences to increase transcription, ribosomal binding site sequences and transcription and translation termination sequences. Alternatively, expression vectors may be capable of directly expressing gene products encoded therein without ligation or integration of the vector into host cell DNA sequences.

The terms "transformed" or "transfected" are used interchangeably and refer to the process by which exogenous DNA or RNA is transferred or introduced into an appropriate host cell. Typically, the exogenous DNA will comprise the promoter regions of this invention, preferably the Flt-1 promoter, operably linked to a heterologous DNA sequence. Such transfected cells include stably transfected cells wherein the inserted DNA is rendered capable of replication in the host cell. Typically, stable transfection requires that the exogenous DNA be transferred along with a selectable marker gene, such as for example, a gene that confers antibiotic resistance, which enables the selection of the stable transfectants. This marker gene may be ligated to the exogenous DNA or be provided independently by simultaneous cotransfection along with the exogenous DNA. Transfected cells also include transiently expressing cells that are capable of expressing the RNA or DNA for limited periods of time. The host cell may be a prokaryotic or eukaryotic cell. The transfection procedure depends on the host cell being transfected. It can include packaging the polynucleotide in a virus as well as direct uptake of the polynucleotide. Transformation can result in incorporation of the inserted DNA into the genome of the host cell or the maintenance of the inserted DNA within the host cell in plasmid form. Methods of transformation/transfection are well known in the art and include, but are not limited to, direct injection, such as microinjection, viral infection, particularly replication- deficient adenovirus infection, electroporation, lipofection, calcium phosphate-mediated direct uptake and the like.

The term "transfer vector" refers to a plasmid that enables the integration of a recombinant gene into virus DNA by homologous recombination.

The term "host cell" generally refers to prokaryotic or eukaryotic organisms and includes any transformable organism which is capable of expressing a protein and can be, or has been, used as a recipient for expression vectors or other transfer DNA. Cells of the vascular endothelium are preferred host cells for expression vectors comprising the VEGF receptor promoters of this invention.

The term "recombinant cells" refers to cells that have been modified by the introduction of heterologous DNA or RNA. Endothelial cells, particularly cells of the vascular endothelium are preferred for introduction of heterologous DNA operably linked to the VEGF receptor promoters of this invention.

It is to be understood that this invention is intended to include other forms of expression vectors, host cells and transformation techniques which serve equivalent functions and which become known to the art hereto.

As noted above, the present invention relates to a recombinant nucleic acid molecule comprising the promoter region of a VEGF receptor. This invention provides a promoter region for tyrosine kinase VEGF receptors, subclass type III, such as Flt-1, Flk-1/KDR and Flt-4, in particular, Flt-1. This invention provides a nucleic acid molecule having a sequence selected from the group consisting of:

(a) the nucleic acid sequence substantially homologous to that of SEQ ID NO: 1 or a fragment thereof, exhibiting promoter activity, in particular Flt-1 promoter activity;

(b) a nucleic acid sequence substantially complementary to said nucleic acid sequence of (a), or a fragment thereof; and (c) a nucleic acid sequence that hybridizes to said nucleic acid sequences of (a) or (b) or fragments thereof.

This invention also provides novel deletion constructs of the VEGF receptor promoter which either increase or decrease promoter activity beyond that of the naturally occurring promoter. The deletion constructs are obtained by deleting from the VEGF receptor promoter sequence shown in FIG. 2 (SEQ ID NO: 1) those segments shown by Applicants to have negative or positive regulatory activity, such as the residues 839 to 862 (residues −356 to −333 of FIG. 2), residues 1479 to 1745 (residues +284 to +550 of FIG. 2), residues 447 to 612 (−748 to −583 of FIG. 2) and residues 956 to 1120 (residues −239 to −75 of FIG. 1) of SEQ ID NO: 1, or portions thereof. The numbering for residue positions used above and elsewhere in the specification refers to the numbering used in FIG. 2 unless stated otherwise. Deletion constructs in which negative regulatory regions have been removed result in enhanced promoter activity. Such constructs provide greater sensitivity than the native promoter when used to screen for drugs which affect VEGF receptor promoter activity.

The nucleic acid molecules of this invention are useful in effecting tissue specific expression in endothelial cells as described in greater detail below and screening for drugs that selectively modulate transcription in endothelial cells and drugs that modulate angiogenic processes.

Preferably, such nucleic acid molecules will be substantially homologous to the nucleic acid sequence shown in FIG. 2 (SEQ ID NO:1), and more preferably to the sequence of residues 447 to 1479 of SEQ ID NO:1 (−748 to +284 of FIG. 2). Substantial homology in the nucleic acid context means that the segments, or their complementary strands, when compared, are the same when properly aligned, with the appropriate nucleotide insertions and deletions, in at least about 60% of the nucleotides, typically, at least about 70%, more typically, at least about 80%, usually; at least about 90%, and more usually, at least, about 95-98% of the nucleotides. Alternatively, substantial homology exists between two segments when the segments or their complementary strands will hybridize under stringent hybridization conditions to a template strand. Selective hybridization exists when the hybridization is more selective than total lack of specificity. See, Kanehisa, *Nucleic Acids Res.*, 12:203–213 (1984).

The nucleic acid sequences provided above can be used by those skilled in the art to practice the invention as disclosed herein without undue experimentation using, for example, Sambrook, Fischer and Maniatis, *Molecular Cloning, a laboratory manual,* (2nd ed.), Cold Spring Harbor Laboratory Press, New York, (1989) and F. M. Ausubel et al eds., *Current Protocols in Molecular Biology,* John Wiley and Sons (1994).

Alternatively, those skilled in the art can practice the invention by repeating the experimental procedures carried out by the inventors and described herein for the isolation and characterization of the VEGF receptor promoters, their transfection into host cells, and vascular endothelial cell-specific expression of heterologous DNA operably linked to said VEGF receptor promoters.

Cloning and Characterization of the Flt-1 Promoter

Restriction Map and Exon-intron Organization of 5'-specific Human Flt-1 Genomic Clones—Genomic clones from a human placental genomic library were obtained by screening with a human Flt-1 cDNA 5'-end 600 bp EcoRI/AccI DNA fragment Three overlapping but not identical genomic clones were selected for further analysis based on the result of Southern analyses using the human Flt-1 cDNA 5'-end oligo DNA probe. The restriction maps of these clones were determined by the partial restriction method and are shown in FIG. 1. The 3 kb EcoRI/XhoI fragments from all three clones were subcloned into pBluescript-KS(+). Detailed restriction maps and partial sequences showed that these 3 kb fragments were identical. Sequence Analysis of the Promoter Region of Flt-1—The nucleotide sequence of a 1.8 kb BstXI/XhoI fragment from clone #4–18 (FIG. 1) was determined by the Sanger dideoxy termination method. This sequence of this fragment is shown in FIG. 2 (SEQ ID NO:1) and contains exon 1, a 5' portion of intron 1, and the 5' flanking region of Flt-1 containing putative transcription factor binding sites such as a TATA box, a CREB/ATF element, and an ETS binding site. The first intron contains a putative transcription arrest site as discussed below.

Figure 3:
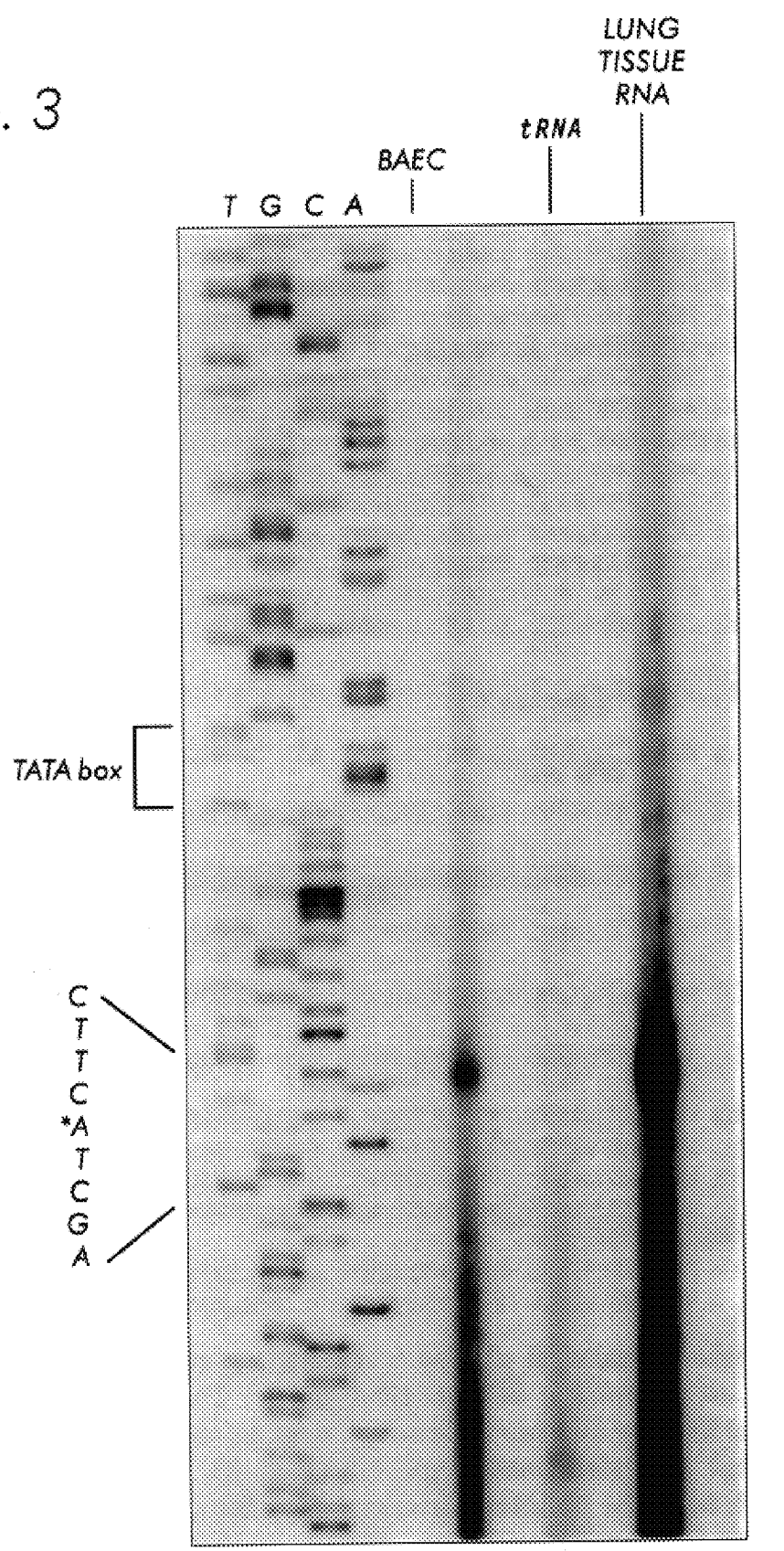
FIG. 3 Identification of the transcription initiation site of Flt-1 by primer extension analysis. Total RNAs from BAEC, yeast tRNA, or lung tissue RNA were analyzed using the synthetic oligonucleotide Oligo-F as a primer. Sequence reactions of the Flt-1 genomic DNA using the same primer were run in parallel. An asterisk indicates the transcription initiation site.

Transcription Initiation Site—To identify the transcription initiation site of Flt-1, primer-extension analysis was performed with total RNA from HUVEC and human lung tissue (FIG. 3). The transcription initiation site was mapped to an adenosine residue 25-bp down-stream from the TATA box. This result was confirmed by S1 mapping analysis.

This invention also provides fragments of the genomic VEGF receptor promoter, which fragments may possess enhanced transcriptional activity relative to the genomic promoter. This invention also provides expression vectors comprising the VEGF receptor promoter, in particular the promoter region of the VEGF receptor, Flt-1, operably linked to a heterologous gene encoding a gene product and host cells transformed or transfected with such expression vectors. The gene product may be a reporter gene, as will typically be the case when the host cells of the invention are being used to screen for expression of the reporter gene in the presence of a putative regulator of the promotional activity of the Flt-1 promoter. Alternatively, the gene product may be a protein, polypeptide, hormone, ribozyme, antisense messenger RNA and the like when endothelial-specific tissue expression of the protein, polypeptide, hormone, ribozyme, antisense messenger RNA and the like is desired.

Figure 4:
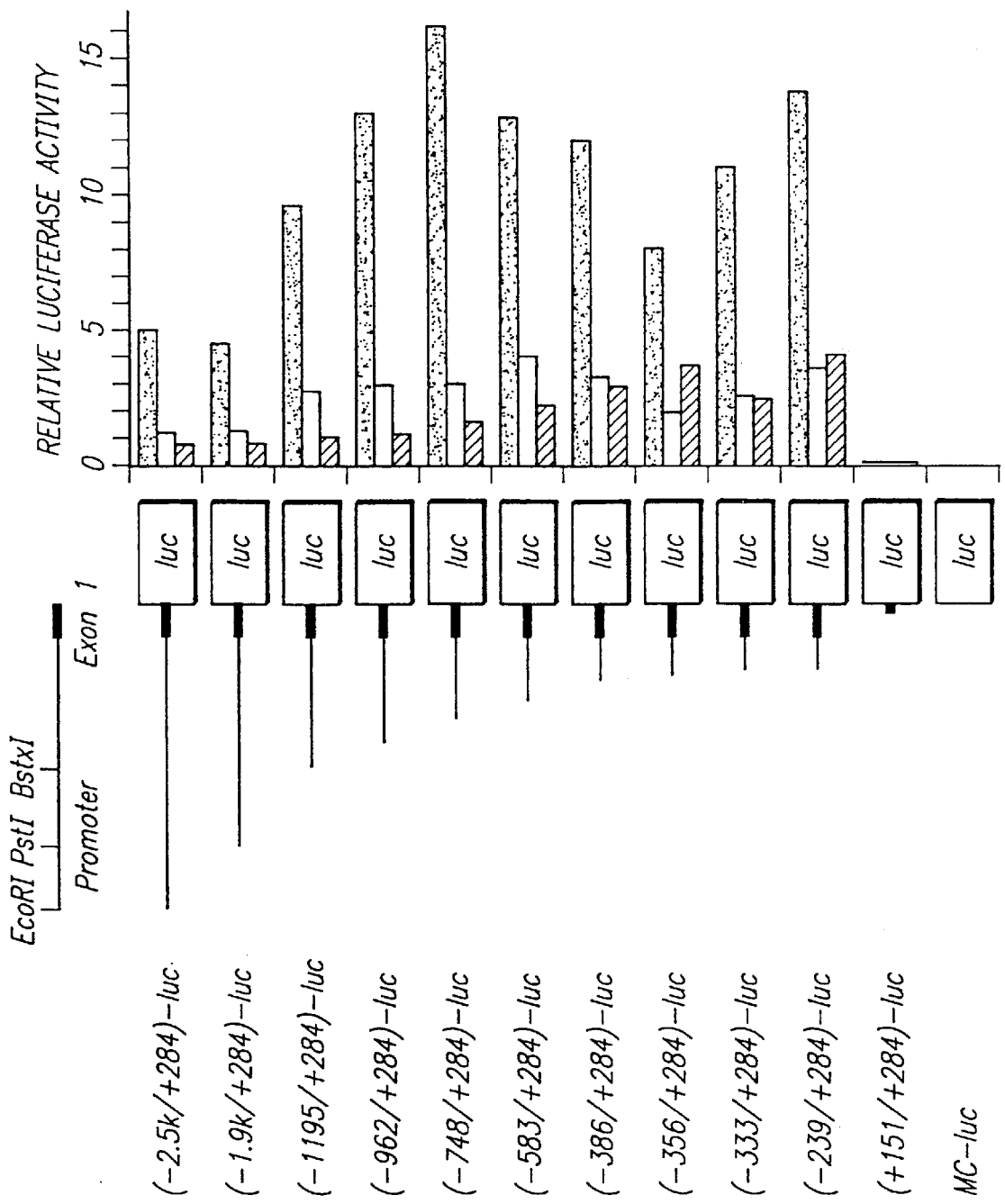
FIG. 4 Expression of luciferase fusion gene constructs containing 5' deleted Flt-1 promoter sequences. The constructs were transiently transfected into BAEC (solid), NIH-3T3 cells (open), and HFF (shaded). Luciferase activities were normalized to internal pSV-CAT control in each extract to adjust for differences in transfection efficiencies. The luciferase activity obtained with transfection of pSV-luc is arbitrarily set at 1 for each cell type. All other luciferase activities are given relative to this value. Each value is the mean of at least three independent experiments.
Figure 6A:
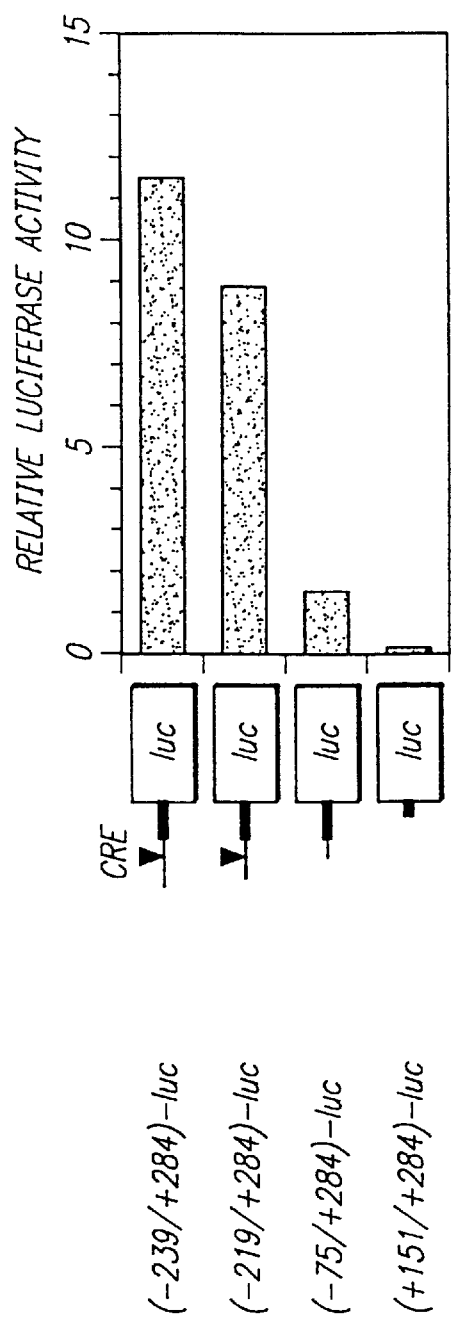
FIGS. 6(A–B) Effect on Flt-1 promoter activity by: (A) further deletion of a 5' flanking region and (B) internal deletion of CREB/ATF element. (A) Constructs containing shorter promoter regions than the constructs shown in FIGS. 4 and 5 were analyzed. (B) Four internal bases of the CREB/ATF element (ACGT out of TGACGTCA) were deleted in ΔCRE(−962/+284)-luc. These constructs were transiently transfected into BAEC. The data are presented in the same manner as in FIG. 4. Each value is the mean of two independent experiments. Filled triangles indicate the CREB/ATF element.

Fragments of the VEGF receptor promoter were obtained by constructing a series of 5'-deletion mutant plasmids fused to the luciferase reporter gene by partial exonuclease digestion. To determine the sequences essential for efficient transcription of the Flt-1 promoter, a DNA construct was prepared by fusing a DNA segment extending from +284 bp to −2.5 kb of the sequence in FIG. 2 to a luciferase gene in the promoterless plasmid pMC-luc vector described in the Examples. This construct, designated as p(−2.5k/+284)-luc, contains 2.5 kb of the promoter region, 230 bp of exon 1, and 54 bp of the 5' end of the first intron, and was used to generate a series of 5' end deletions (FIGS. 4 and 6A). The resultant constructs are referred to as p(X/Y)-luc. For each, X and Y represent the 5'- and 3'-end position respectively in the nucleotide sequence with reference to the numbering used in FIG. 2. Several 5'-deletion mutants were produced: p(−962/+284)-luc, p(−748/+284)-luc, p(−583/+284)-luc, p(−386/+284)-luc, p(−356/+284)-luc, (−333/+284)-luc, p(−239/+284)-luc, p(−219/+284)-luc, p(+151/+286)-luc and p(−75/+284)-luc. Each construct was transfected into bovine adrenal endothelial cells (BAEC), murine fibroblast NIH-3T3 cells and human foreskin fibroblast cells (HFF) and promoter activity was assessed by measuring luciferase activity.

Promoter activity of these deletion mutants in BAEC, NIH-3T3 and HFF is shown in FIG. 4. Deletion mutant p(−748/+284)-luc showed the highest activity. Transfection of the series of constructs deleted from −2.5 kb to +151 showed the presence of at least two regions, 2500 to −1195 and −356 to −333, containing negative regulatory sequences, and two regions, −748 to −583 and −239 to −75, containing positive regulatory sequences. Deletion to +151 decreased luciferase activity to the level of the promoterless plasmid pMC-luc.

Figure 7:
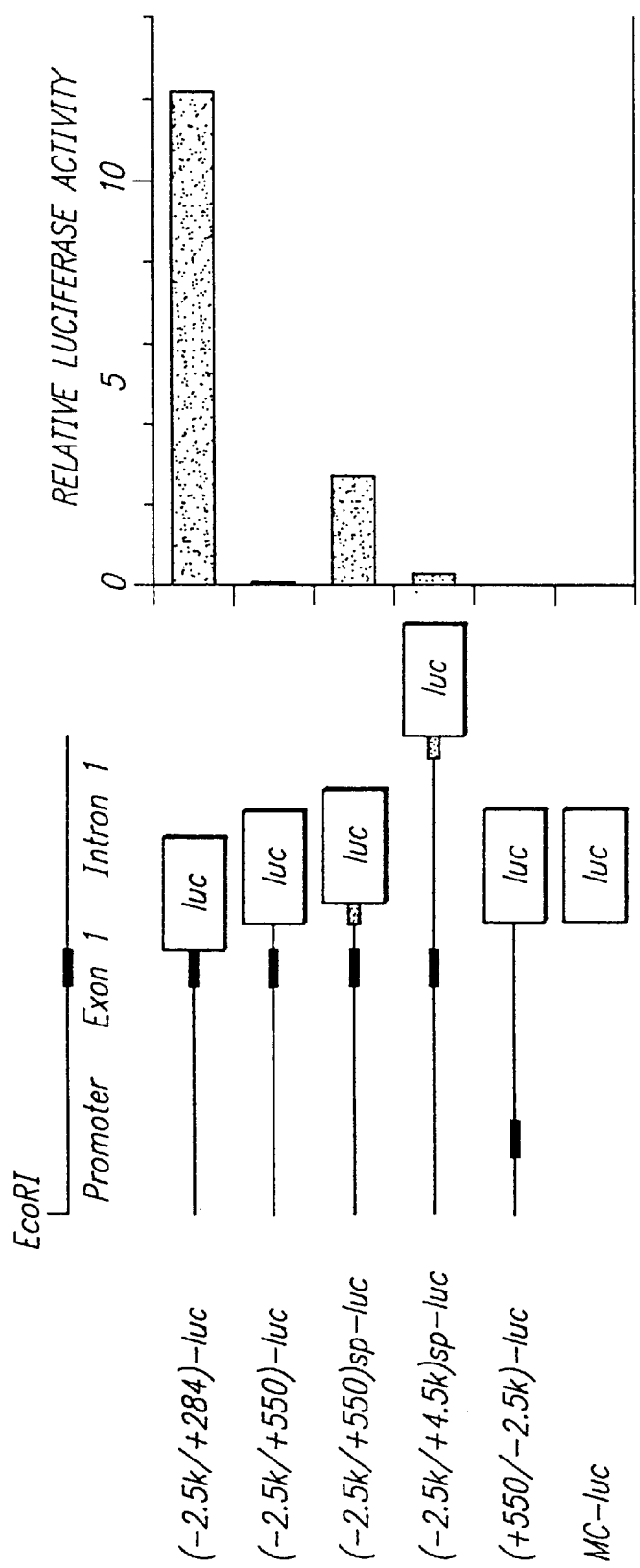
FIG. 7. Negative effect of intron 1 on the Flt-1 promoter activity. Both (−2.5k/+550)sp-luc and (−2.5k/+4.5k)sp-luc contain a hybrid intron consisting of 220 bp or 2.3 kb of the 5' portion of the first intron of Flt-1 and a 3' splice site of a mouse immunoglobulin gene. By contrast, (−2.5k/+550)-luc contains only 220 bp of the 5' portion of the first intron of Flt-1. (+550/−2.5k)-luc has the promoter oriented in the reverse direction. These constructs were transiently transfected into BAEC. The data are presented in the same manner as in FIG. 4. Each value is the mean of two independent experiments. The shaded box indicates a 3' splice site of a mouse immunoglobulin gene.

Transfection of the p(−2.5k/+550)-luc construct, which contains 220 bp of the first intron of flt-1 (containing the 5' splice site but not the 3' splice site), resulted in no luciferase activity (FIG. 7). There are several mechanisms by which introns have been shown to regulate gene expression: 1) transcriptional attenuation by a silencer, 2) formation of double-stranded RNA by antisense transcripts (Krystal, G., Armstrong, B. C., and Battey, J. F. (1990) *Mol. Cell. Biol.* 10, 4180–4191; Kimelman, D. and Kirschner, M. W. (1989) *Cell* 59, 687–696), and 3) transcription arrest (Kash, S. F., Innis, J. W., Jackson, A. U., and Kellems, R. E. (1993) *Mol. Cell. Biol.* 13, 2718–2729). In the case of flt-1, the first intron contains a sequence which is very similar to the transcription arrest site in the first intron of adenosine deaminase (ADA) gene (FIG. 8). Thus, it appears that the negative regulation conferred by intron 1 may be due to transcriptional arrest.

In conclusion, it has been shown in a series of transfection assays that a 1 kb DNA fragment of the 5'-flanking sequence of Flt-1 has functional activity in vascular endothelial cells but limited activity in epithelial cells, vascular smooth muscle cells, and fibroblasts. It has also been shown that the Flt-1 CREB/ATF element was essential for basal transcription and the first intron of Flt-1 negatively regulated gene expression.

Endothelial Cell Specificity of the Flt-1 Promoter

This invention also provides methods for tissue-specific expression of heterologous genes or DNA in endothelial cells, particularly in vascular endothelial cells, employing the Flt-1 promoter. Convention drug delivery technology is not amenable to tissue specific delivery of bioactive species. For example, direct delivery of cytokines such as IL-2, TNFα and gamma interferon has been hampered by their low half life, poor bioavailability and high toxicity. This invention provides methods of directly delivering bioactive species to endothelial cells, particularly vascular endothelial cells, via their specific endogenous production in the endothelium. The vectors provided by this invention are useful for the tissue specific expression of genes useful for treating diseases affecting the vascular endothelium such as, but not limited to, hypertension, thrombosis, atherosclerosis and restenosis. Inflammatory diseases characterized by endothelial cell activation should also be susceptible to inhibition by genes delivered via the vectors of this invention.

The tissue specific regulatory sequences present in human genomic DNA, as described herein, can also be used to target endothelial cells for killing. Thus, tumor cells or infected cells can be targeted for death, as has been done using antibodies specific for the tumor cell or the infected cell to deliver a toxic agent to the diseased cell. As described above, the preferred regulatory-sequence for liver or kidney specific expression includes the promoter regions of the VEGF receptor of the present invention.

The regulatory sequences can be used to target expression of a "toxic" peptide of bacterial, plant or animal origin (Frankel, A. E. et al., Ann. Rev. Med. 37:125–142 (1986)) to an endothelial cell, preferably in the vascular endothelium. Any of a number of toxic proteins of bacterial origin, such as Pseudomonas exotoxin A or Diphtheria toxin (Endo, Y. et al., J. Biol. Chem. 262:5908–5912 (1987)) are known. Examples of well-known toxic proteins, primarily single chain ribosomal inhibitory proteins, of plant origin, include ricin or abrin A chain, Trichosanthin (Gu, Z. et al., Acta Chemica Sinica 43:943–945 (1984)) and the non-toxic anti-HIV protein, TAP 29, derived therefrom (Lee-Huang, S. et al. Proc. Natl. Acad. Sci. (USA), 88:6570–6574 (1991)), GLQ 223 isolated from T. kirilowil (McGrath, M. S. et al., Proc. Natl. Acad. Sci. (USA) 86:2844–2848 (1989)), momordica-derived inhibitors (Jimenez, A. et al., Annu. Rev. Microbiol. 39:649–672 (1985)) including MAP 30, an anti-tumor and anti-viral protein recently isolated in the laboratory of the present inventor from Momordica charantia (Lee-Huang, S. et al., FEBS Lett. 272:12–18 (1990)), the pokeweed anti-viral proteins (PAP) (Irvin, J. D. et al., Arch. Biochem. Biophys. 200:418–425 (1980)), dianthins (Stripe, F.et al., Biochem. J. 295:399–405 (1981)) and gelonin (Stripe,F.et al., L7. Biol. Cbem. 255:6947–53 (1980)). Also intended are a new class of anti-HIV agents, GAP 31, DAP 32 and DAP 30 (Lee-Huang, S. et al. FMS Lett. 291:139–144 (1991); Lee-Huang, S. et al., Biofactors 4:37–41 (1992)). An animal-derived toxic protein is tumor necrosis factor-$\alpha$. Such toxic proteins may act as antiviral agents or an antitumor agents.

The regulatory sequences of the present invention may also be used to target an antisense oligonucleotide (Hambor, J. E. et al., J. Exp. Med. 168:1237–1245 (1988) Holt, J. T. et al., Proc. Nat'l. Acad. Sci. 83:4794–4798 (1986); Izant, J. G. et'al., Cell 36:1007–1015 (1984); Izant, J. G., et al., Science 229:345–352 (1985) and De Benedetti, A. et al., Proc. Natl. Acad. Sci. 84:658–662 (1987)), for example, of a specific oncogene, to the liver or kidney and to kill the respective tumor cells. The antisense oligonucleotides may range from 6 to 50 nucleotides, and may be as large as 100 or 200 nucleotides. The oligonucleotides can be DNA or RNA or chimeric mixtures or derivatives or modified versions thereof, single-stranded or double-stranded. The oligonucleotides can be modified at the base moiety, sugar moiety, or phosphate backbone.

Examples of using various tissue specific regulatory sequences, as disclosed herein, for targeted expression and for killing of specific cells are known in the art, including expression of (1) SV40 large T antigen in pancreatic 0 cells by insulin regulatory sequence (Hanahan, D., Nature 315:115–122 (1985), (2) diphtheria toxin A chain in pancreas by elastase I regulatory sequence (Palmiter, R. D. et al., Cell, 50:435–443 (1987), and (3) ricin or diphtheria toxin A chain in lens cells by the tissue specific regulatory sequence of crystallin genes (Borrelli, E. R. et al., Proc. Natl. Acad. Sci. (USA) 85:7572–7576 (1988)).

When used in such tissue specific applications, the expression vectors of this invention can be used to express heterologous genes in addition to luciferase or chloramphenicol transferase. Generally, in addition to the heterologous gene operably linked to the VEGF receptor promoter sequences of this invention, the vector will contain at least one eukaryotic marker gene, the appropriate eukaryotic transcriptional and translational stop signals, at least one Shine-Delgarno sequence and initiator codon, a signal that signals polyadenylation of the transcribed mRNA, and any other DNA sequences necessary or preferred for the appropriate transcription and translation of the heterologous DNA. These additional sequences may include a signal sequence for proteins to be exported or secreted from the host cell and at least one gene for a transcriptional regulator protein. If the vector is used as an extrachromosomal replicating DNA in the eukaryotic cell where it is expressed, the vector will include an origin of replication that functions in the host cell. When the vector is to be integrated into the host chromosomal DNA, it will contain elements necessary to facilitate its integration into the host genome. These elements may be provided by viral vectors such as vaccinia and adenovirus, or by nonviral recombinant plasmids.

DNA is commonly transferred or introduced into recipient mammal cells by calcium phosphate-mediated gene transfer, electroporation, lipofection, viral infection and the like. General methods, vectors and general considerations for gene transfer and expression may be found in M. Kriegler, *Gene Transfer and Expression: A Laboratory Manual,* Stockton Press (1990). Direct gene transfer to cells in vivo is achieved by the use of modified viral vectors, including retroviruses, adenoviruses, adeno-associated viruses and herpes viruses, liposomes, and direct injection of DNA into certain cell types. In this manner, recombinant expression vectors and recombinant cells containing the novel VEGF promoters of the present invention operably linked to desired heterologous gene can be delivered to specific target cells in vivo. See, e.g., Wilson, Nature, 365: 691–692 (1993); Plautz et al, Annals NY Acad. Sci., 716: 144–153 (1994); Farhood et al, Annals NY Acad. Sci., 716: 23–34 (1994) and Hyde et al Nature, 362: 250–255 (1993). Furthermore, cells may be transformed ex vivo selected as described earlier and introduced directly at localized sites by injection, e.g., intra-articular, intracutaneous, intramuscular and the like.

Another aspect of this invention also provides methods of inhibiting angiogenesis of a tumor by transfecting endothelial cells lining the tumor with a vector comprising a nucleic acid sequence for a VEGF receptor promoter, preferably the Flt-1 promoter, operably linked to a gene that codes for a species that inhibits vascular permeability or has antimitogenic activity. Expression of such species prevent vascularization of the tumor, block nutrient access to the tumor and thereby inhibit tumor growth. The encoded species may be peptides, proteins, hormones, ribozymes, antisense RNA, and the like. Ex vivo transfection methods for delivering the species to the tumor may be used. Such methods generally involve explanting cells from the mammal, transfecting the cells with an expression vector comprising a nucleic acid comprising a VEGF receptor promoter operatively linked to gene coding for the desired species and selecting and reimplanting into the mammal cells which have incorporated and express said nucleic acid. In vivo transfection can be accomplished by methods such as direct injection of the above expression vectors.

Another aspect of the invention provides methods of inhibiting thrombogenesis in a mammal by transfection of vascular endothelial cells with an expression vector comprising the novel promoter sequences of this invention operably linked to a gene that encodes for a protein that inhibits thrombogenesis by, for example, enhancing fibrinolysis or increasing the anticoagulability of blood. In general, thrombus formation occurs on the surface of vascular endothelial cells. Thus, endothelial cells are a good target for expression of such proteins. The tissue-specific expression made possible by the VEGF receptor promoters disclosed herein, particularly the Flt-1 promoter, provides a method for preferentially expressing these proteins in vascular endothelial cells. Proteins whose expression can be placed under the regulatory control of the promoter sequences for the purpose of inhibiting thrombogenesis include, but are not limited to:

(1) Tissue plasminogen activator (t-PA), urokinase (u-PA), single chain urokinase (scu-PA) which enhances fibrinolysis by converting plasminogen to plasmin which in turn degrades the fibrin clot, (2) Antithrombin III (ATIII), which inhibits thrombin and Factor Xa; Tissue Factor Pathway Inhibitor (TFPI), which inhibits Factor Xa; and Thrombomodulin, which activates Protein C, which, once activated, destroys Factor Va and Factor VIIIa, all of which inhibit blood coagulation. Proteins that inhibit platelet aggregation may also be linked to the promoters of this invention for the purpose of inhibiting thrombogenesis.

Conversely, the blood coagulation pathway can also be affected by the vascular endothelial cell-specific expression of proteins such as Factor VIII and Factor V which enhance clot formation, i.e., increase coagulation, thereby allowing the treatment of hemophilia and related diseases.

Treatment of the above described conditions by expression of such proteins can be accomplished by injection of an expression vector of the VEGF receptor promoter operably linked to the genes encoding the proteins described above. The method of injection can be by bolus or localized injection by catheter and the like.

Construction of expression vectors containing the novel promoter sequences, such as the Flt-1 promoter sequence and its substantially homologous complements, operably linked to DNA sequence encoding a gene product and capable of expressing said gene product when transfected into a target host cell can be accomplished by methods known to one of skill in the art. Typically the promoter and the DNA sequence encoding the desired gene product will be cloned into an expression vector via suitable restriction endonuclease sites such that the promoter is upstream of and in-frame with the DNA sequence. The expression vector may be a plasmid, virus or a cosmid. The cloned expression vector may then be transfected into the target host cells and successfully transformed cells may be selected based on the presence of a suitable marker gene as described earlier.

Figure 5:
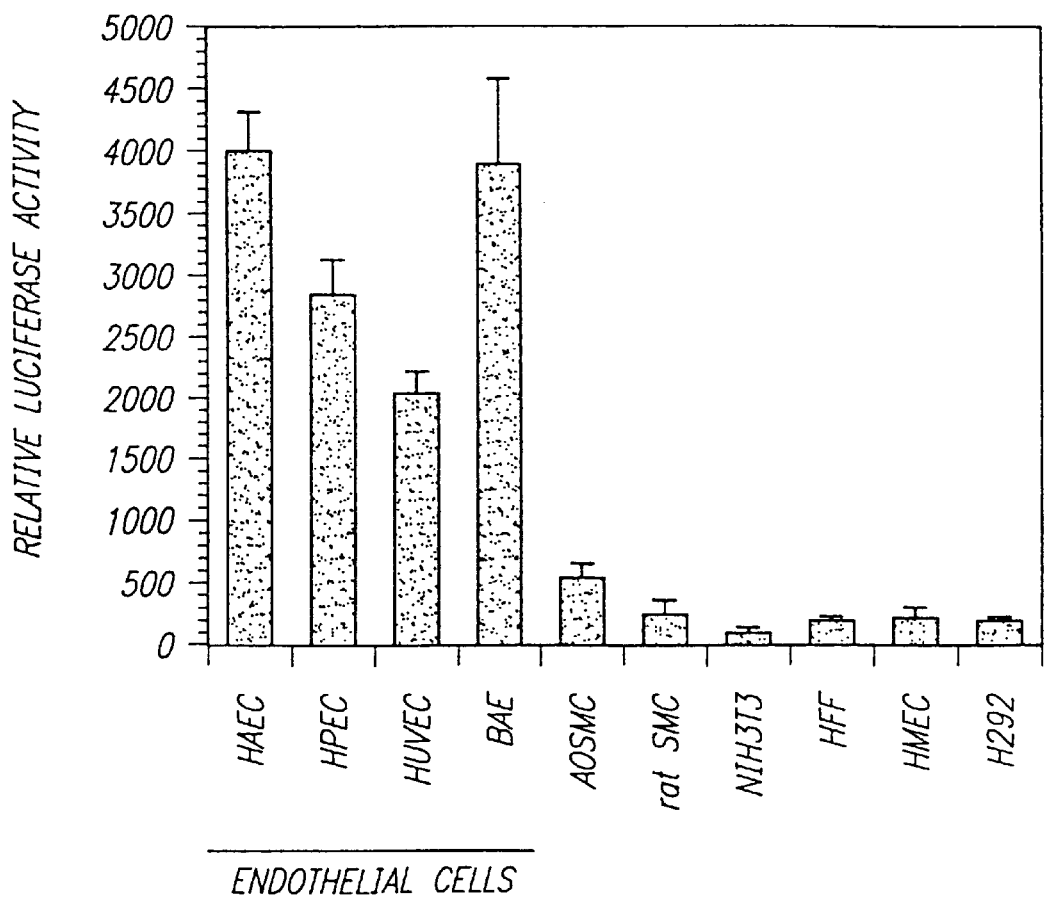
FIG. 5. Expression of the Flt-1 promoter (−748/+284)-luciferase fusion gene in various human primary cells and established cell lines. The replication-deficient recombinant adenovirus AdexFLTP-luc carrying the Flt-1 promoter (−748/+284)-luciferase-fusion gene and AdexCAlLacZ were co-infected into various human primary endothelial cells (HAEC, HPEC, HUVEC) bovine adrenal endothelial cells (BAE), human primary mammary epithelial cells (HMEC), human primary aortic smooth muscle cells (AOSMC), NCI-H292 cells, human Loreskin fibroblasts (HFF), rat primary aortic smooth muscle cells (rat SMC), and NIH-3T3 cells. Luciferase activities were normalized to b-galactosidase activities in each extract. Each value is the mean of at least three independent experiments.

Endothelial cell specificity of the Flt-1 promoter was shown by transfection of the 5'-deletion mutants described above into murine fibroblast NIH-3T3 cells and HFF cells and comparing luciferase activity to BAEC transfected cells. As shown in FIG. 4, relative luciferase activities in NIH-3T3 and HFF cells were much weaker than those in BAEC. The endothelial specificity of the Flt-1 promoter was further demonstrated by transfection of the 5'-deletion mutants into various human primary cells. The Flt-1 promoter (−748/+284)-luciferase-fusion gene construct was introduced into human cells using a replication-deficient recombinant adenovirus. The recombinant adenovirus AdexFLTP-luc carrying the Flt-1 promoter (−748/+284)-luciferase-fusion gene was used to infect various human primary cells and established cell lines. Following infection, relative luciferase activities seen in human primary endothelial cells such as aortic endothelial cells, pulmonary arterial endothelial cells, umbilical vein endothelial cells, and bovine adrenal endothelial cells were much higher than activities seen in human primary mammary epithelial cells, human primary aortic smooth muscle cells, NCI-H292 cells, human foreskin fibroblasts, rat primary aortic smooth muscle cells, and NIH-3T3 cells (FIG. 5). These results showed that the Flt-1 promoter region between positions −748 and +284 (residues 447 to 1479 of SEQ ID NO:1) conferred endothelial-specific gene expression.

Thus this invention provides compositions for and methods of endothelial-specific tissue expression of heterologous DNA. Such endothelial-specific gene expression is useful in the study of and therapy for diseases involving the vascular system, e.g., hemostasis, wound healing, atherosclerosis, hypertension, diabetic retinopathy, rheumatoid arthritis, blood cell trafficking, inflammatory conditions and tumor angiogenesis. The heterologous DNA may encode for proteins, polypeptides, hormones, antisense mRNA and the like. The proteins and polypeptides that may be expressed include cellular adhesion molecules, cytokines, hormones, growth factors, enzymes, clotting factors, apolipoproteins, receptors, drugs, inhibitors of intra- and extra-cellular processes, antigens and oncogenes. Specific examples include TNFα, IL-2, granulocyte macrophage colony stimulating factor (GM-CSF), insulin like growth factor, tissue plasminogen activator, mutant VEGF receptors and the like. Thus, this invention provides methods of selective targeting and expression of such antitumor agents such as IL-2 and TNFα directly to cancerous tissue thus directly activating cytotoxic lymphocytes at the tumor site. Endothelial cell specific-transcription of antisense mRNA against Flt-1 may be employed to inhibit and prevent VEGF receptor expression, thus preventing tumor angiogenesis and tumor growth. Alternatively, endothelial specific expression of soluble VEGF receptor mutants capable of binding VEGF but incapable of stimulating endothelial cell mitogenesis such as those described in WO 94/21679 provides a specific method of controlling tumor proliferation and inhibiting tumor angiogenesis.

Host cells provided by this invention expressing heterologous genes under the control of the promoter sequences of this invention can be used to produce proteins, preferably human proteins and fragments thereof. The process involves culturing the transformed cell under conditions wherein the protein is expressed, optionally by inducing the activity of the promoter, and purifying the protein from the cell culture. Purification generally involves the steps of cell lysis, homogenization, centrifugation and separation of the desired protein by processes such as salt fractionation, precipitation, and a variety of chromatographic methods such as anion exchange chromatography, hydrophobic interaction chromatography, high resolution chromatography, gel filtration chromatography and the like.

Drug Screening

Another aspect of this invention is its use in screening for pharmacologically active agents that modulate of VEGF receptor promoter activity, particularly for receptors of the type III subclass, and more particularly, Flt-1, either by affecting signal transduction pathways that necessarily precede transcription or by directly affecting transcription of the VEGF receptor.

For screening purposes an appropriate host cell, preferably an endothelial cell, more preferably a vascular endothelial cell, is transformed with an expression vector comprising a reporter gene operably linked to the VEGF receptor promoter of this invention. The transformed host cell is exposed to various test substances and then analyzed for expression of the reporter gene. This expression can be compared to expression from cells that were not exposed to the test substance. A compound which increases the promoter activity of the VEGF receptor promoter will result in increased reporter gene expression relative to the control. Similarly, compounds which act as antagonists for the VEGF receptor signalling pathway will result in decreased reporter gene expression relative to the control.

Thus in one aspect of the invention one can screen for test compounds that regulate the activity of the VEGF receptor promoter by:

(a) contacting a host cell in which the VEGF receptor promoter disclosed herein is operably linked to a reporter gene with a test medium containing the test compound under conditions which allow for expression of the reporter gene;

(b) measuring the expression of the reporter gene in the presence of the test medium;

(c) contacting the host with a control medium which does not contain the test compound but is otherwise identical to the test medium in (a), under conditions identical to those used in (a);

(d) measuring the expression of reporter gene in the presence of the control medium; and (e) relating the difference in expression between (b) and (d) to the ability of the test compound to regulate the activity of the VEGF receptor promoter.

Alternatively, the transformed cells may be induced with a transcriptional inducer, such as IL-1 or TNFα, forskolin, dibutyryl-cAMP, or a phorbol-type tumor promoter, such as, for example PMA. Transcriptional activity is measured in the presence or absence of a pharmacologic agent of known activity (i.e., a standard agent) or putative activity (i.e., a test agent). A change in the level of expression of the reporter gene in the presence of the test agent is compared to that effected by the standard agent. In this way, the ability of a test agent to affect VEGF receptor transcription and their relative potencies can be determined.

Thus one aspect of this invention provides methods of measuring the ability of a test compound to modulate VEGF receptor transcription by:

(a) contacting a host cell in which the VEGF receptor promoter disclosed herein is operably linked to a reporter gene with an inducer of VEGF receptor promoter activity under conditions which allow for expression of the reporter gene;

(b) measuring the expression of the reporter gene in the absence of the test compound;

(c) exposing the host cells to the test compound either prior to, simultaneous with, or after contacting, the host cells with the inducer;

(d) measuring the expression of the reporter gene in the presence of the test compound; and (e) relating the difference in expression between (b) and (d) to the ability of the test compound to modulate VEGF receptor transcription.

Since different inducers are known to affect different modes of signal transduction (e.g., cAMP responsive, calcium ion responsive), it is possible to identify with greater specificity compounds which affect a particular signal transduction pathway. Furthermore, since the VEGF receptors, particularly Flt-1, has been shown to be upregulated in tumor cells and this upregulation is necessary for tumor angiogenesis, such assays provide a means of identifying compounds which will inhibit and/or reverse tumor growth by downregulating Flt-1 and thus preventing tumor angiogenesis.

In another aspect of this invention, transgenic animals expressing a heterologous gene encoding a detectable product under the regulatory control of the VEGF receptor promoter disclosed herein may be used to determine the effect of a test compound on the stimulation or inhibition of the VEGF receptor promoter. The test compound is administered to the animal and the degree of expression of the heterologous gene observed is compared to the degree of expression in the absence of administration of the test compound using routine bioassays as disclosed herein.

A variety of reporter genes may be used. Preferred are those which produce a protein product that is easily measured in a routine assay. Suitable reporter genes include but are not limited to chloramphenicol acetyl transferase, luciferase and β-galactosidase. Convenient assays are calorimetric, fluorimetric and enzymatic assays. Most preferred are reporter genes that are expressed within the cell and whose extracellular products are directly measured in the intracellular medium, or in an extract of the intracellular medium of a cultured cell line. This provides advantages over using a reporter gene whose product is secreted, since the rate and efficiency of the secretion introduce additional variables which complicate interpretation of the assay.

The host cells transformed with the novel promoter sequences of this invention can also be used to identify compounds which specifically bind the VEGF receptor and act as agonists or antagonists of the VEGF receptor. As described earlier, deletion constructs of the VEGF receptor promoter can be employed to increase VEGF receptor expression and increase the sensitivity of the assay. This method comprises:

(a) incubating a host cell transformed with a VEGF receptor promoter of SEQ ID NO: 1, or fragment thereof operably linked to a VEGF receptor gene with a test compound and a labelled VEGF;

(b) measuring the amount of labelled VEGF which binds to the cell; and (c) comparing the amount bound in (b) to the amount of VEGF that binds to the cell in the absence of the test compound and relating the difference in these two amounts to the test compound being an antagonist or agonist of the VEGF receptor regulatory system.

Transgenic Animals

This invention also provides transgenic animals useful as disease models for studying VEGF receptor function and endothelial cell-specific gene expression.

Transgenic animals with genes comprising the VEGF receptor promoters operably linked to a heterologous gene can be prepared by methods known to those of skill in the art such as, but not limited to, B. Hogan et al, *Manipulating the Mouse Embryo,* Cold Spring Harbor Laboratory Press, New York (1986) and U.S. Pat. No. 5,162,215, R. A. Bosselman et al, *Method of Gene Transfer into Chickens and other Avian Species* (1992).

Briefly, using mice as an example, fertilized eggs are collected by washing out the oviducts of mated females and a DNA construct of the VEGF receptor promoter operably linked to a heterologous DNA sequence is microinjected into the pronuclei. The injected eggs are then transferred to and implanted in the uterus of foster mothers, female mice made pseudopregnant by mating with vasectomized males. After birth the progeny mice are checked for presence of the transgene by Southern blotting of DNA extracted from a small piece of the tail. If suitable primers are available, screening can be rapidly performed by polymerase chain reaction. The transgene may be integrated into the germ line cell, somatic cells or both. Transgenic mice carrying the transgene in their germ line cells can be identified by mating them with normal nontransgenic mice and determining whether the inheritance of the transgene follows expected Mendelian genetics. This is often conveniently accomplished by including in the injected DNA construct a gene coding for readily visible trait such as skin coat color. An alternative method of transgenic animal production involves injecting a DNA construct comprising the novel VEGF receptor promoters of this invention into undifferentiated embryonic stem cells prior to injecting into the mouse blastocyst.

Such transgenic animals provide an animal model for human diseases. This is particularly important for modelling diseases where no good animal model exists because the pathogen is specific for a human host. Endothelial cell-specific gene expression of pharmacologically active proteins in transgenic animals allows one to study and identify therapeutically agents for the treatment of human disease in an animal model. The animals carrying genes comprising the VEGF receptor promoter sequences disclosed herein can be used to test for compounds which modulate gene expression in vivo, in particular by regulating the promoter activity of the VEGF receptor. As described earlier, vascularization of solid tumor masses are characterized by upregulation and increased expression of the VEGF receptor, particularly Flt-1. Thus such transgenic animals may be used to identify compounds which reverse this upregulation.

Introduction of the desired DNA sequence at the fertilized oocyte stage ensures that the transgene is present in all of the germ cells and somatic cells of the transgenic animal and has the potential to be expressed in all such cells. The presence of transgene in the germ cells of the transgenic "founder" animal means that all of its progeny will in turn carry the transgene in all of their germ line and somatic cells. Conversely, introduction of the transgene at a later embryonic stage in a founder animal may result in limited presence of the transgene in some somatic cell lineages of the founder animal. Chimeric animals in which fewer than all of the somatic and germ cells contain the transgenic DNA sequence of the present invention, produced for example, when fewer than all of the cells of the morula are transfected in the process of producing the transgenic animal are also within the scope of the present invention.

Transgenic animals may also be used as bioreactors for the production of large amounts of a desired proteins. Production of certain physiologically active proteins which require unique glycosylation patterns for correct folding and processing may require their expression in specific mammalian cells. In particular, the promoter sequences of this invention may be used to direct the production of a heterologous gene operably linked to the promoter in endothelial cells.

EXAMPLES

The following examples are given to enable those of skill in the art to more clearly understand and practice the invention. They should not be considered as limiting the scope of the invention, but merely illustrative and representative thereof.

Materials

The recombinant adenovirus Adex1CA lacz, the adenovirus cosmid vector pAdex1W and EcoT22I-digested adenoviral DNA—terminal protein complex (TPC) were prepared as described in Y. Nakamura et al., *Cancer Research*, 54, 5757–5760 (1994).

Bovine adrenal endothelial cells (BAEC) were obtained from Dr. Richard Weiner at University of California, San Francisco, and maintained in Dulbecco's modified essential medium (DMEM) supplemented with 1 mg/ml glucose, 1 ng/ml bFGF (basic fibroblast growth factor), and 10% fetal bovine serum (FBS). Human umbilical vein endothelial cells (HUVEC), human aortic endothelial cells (HAEC), human pulmonary arterial endothelial cells (HPEC), human aortic smooth muscle cells (AOSMC), and human mammary epithelial cells (HMEC) were obtained from Clonetics and maintained according to the manufacturer's recommendation. NIH-3T3 cells and human foreskin fibroblasts (HFF) were maintained in DMEM (Dulbecco's modifiec essential medium) supplemented with 10% FBS. NCI-H292 human pulmonary mucoepidermoid carcinoma cells were maintained in RPMI 1640 supplemented with 10% FBS. Rat aortic smooth muscle cells (Sprague-Dawley rats) were isolated from explants as described by Ross, R. (1971) *J. Cell Biol.*, 50, 172–186 and maintained in DMEM supplemented with 10% FBS.

Abbreviations dNTPs, DNTP mix, deoxynucleotide triphosphates; HUVEC, human umbilical vein endothelial cells; BAEC, bovine adrenal endothelial cells; HAEC, human aortic endothelial cells; HPEC, human pulmonary arterial endothelial cells; AOSMC, human aortic smooth muscle cells; HMEC, human mammary epithelial cells; HFF, human foreskin fibroblast; TPC, terminal protein complex; CAT, chloramphenicol acetyltransferase; CREB, cAMP response element binding protein; ATF, activating transcription factor; IBMX, 3-isobutyryl-1-methylxanthine; DMEM, Dulbecco's modified essential medium; FBS, fetal bovine serum; bFGF, basic fibroblast growth factor; VEGF, vascular endothelial growth factor; AMV, avian myeloblastosis virus; kb, kilobase pairs; bp, base pairs: PBS, phosphate buffered saline: DTT, dithiothreitol.

Example 1

Cloning of the 5'-flanking Region of the Human Flt-1 Gene

A human placenta genomic library in EMBL-3 phage (Clontech, Palo Alto, Calif.) was screened with a 600 bp EcoRI/AccI fragment from the 5' end of the Flt-1 cDNA. (Peters, K. G., De Vries, C., and Williams, L. T. (1993) *Proc. Natl. Acad. Sci. USA* 90, 8915–8919; De Vries, C., Escobedo, J. A., Ueno, H., Houck, K., Ferrara, N., and Williams, L. T. (1992) *Science* 255, 989–991 and M. Shibuya et al., *Oncogene*, 5, 519 (1990)). After three rounds of screening, 13 positive clones were isolated. Two sets of overlapping synthetic oligonucleotides, 5'-GGACACTCCTCTCGGCTCCTCCCCGGCAGCGGC GGCGGCTCGG-3'(oligo-E) (SEQ ID NO:3) and 5'-CGCTGGCCGCTGCACCCGAGCCCCGGAGCCCG CTCCGAGCCGCCGC-3' (oligo-F) (SEQ ID NO:4), corresponding to the 5' end of the Flt-1 cDNA between positions +3 and +79 (designated as probe A) and 5'-GGTCTTTGCCTGAAATGGTGAGTAAGGAAAGCG AAAGGCTGAGCATAACT-3' (oligo-J) (SEQ ID NO:5) and 5'-CAGAATTGTTTGCCATTTCTTCCACAGGCAGAT TTAGTTATGCTCAGCCT-3' (oligo-K) (SEQ ID NO:6) corresponding to the sequence of the Flt-1 cDNA between positions +427 and +502 (designated as probe B) were annealed, followed by filling-in with Klenow fragment in the presence of [a-$^{32}$P]dCTP. Four of the 13 clones hybridized with probe A, but not with probe B. In contrast, the other clones hybridized with probe B, but not with probe A. Three different clones which hybridized with probe A were selected for restriction endonuclease and Southern blot analyses. The restriction maps of these clones were determined by the partial restriction method and is shown in FIG. 1. The 3 kb EcoRII/XhoI fragments from all three clones and a 7 kb EcoRI fragment from clone #5–11 were subcloned into Bluescript KS+ (Stratagene, La Jolla, Calif.) to generate pBKS3.0 and pBKS7.0. These plasmids were used for further restriction enzyme mapping, nucleotide sequencing analysis, subcloning, and expression studies as described below.

Detailed restriction maps and partial sequences showed that these 3 kb fragments were identical. The nucleotide sequence of a 1.8 kb BstXI/XhoI fragment from clone #4–18 (FIG. 1) was determined by the Sanger dideoxy termination method. This fragment contains exon 1, a 5' portion of intron 1, and the 5' flanking region of Flt-1 containing putative transcription factor binding sites such as a TATA box, a CREB/ATF element, and an Ets binding site (FIG. 2). The first intron contains a putative transcription arrest site as discussed below.

Transcription Initiation Site—To identify the transcription initiation site of Flt-1, primer-extension analysis was performed with total RNA from HUVEC and human lung tissue (FIG. 3). The transcription initiation site was mapped to an adenosine residue 25-bp down-stream from the TATA box. This result was confirmed by S1 mapping analysis (data not shown). Primer Extension and S1 Mapping—Primer extension analysis was carried out according to described methods (Sambrook, J., Fritsch, E. F., and Maniatis, T. (1989) *Molecular Cloning: A Laboratory Manual*, 2nd Ed., Cold Spring Harbor Laboratory, Cold Spring Harbor, N.Y.). Briefly, oligo-F was end-labeled with T4 polynucleotide kinase. Approximately 5 ng of labeled primer was hybridized to 50 mg of total RNA from HUVEC, human lung tissue (Clontech, Palo Alto, Calif.), and yeast tRNA in Hybridization buffer (80% formamide/40 mM PIPES (pH 6.4)/400 mM NaCl/ mM EDTA) at 30° C. overnight. The extension reaction was carried out with 50 units of AMV reverse transcriptase (Promega, Madison, Wiss.) in 50 mM Tris-HCl (pH 7.6)/60 mM KCl/10 mM $MgCl_2$/1 mM dNTPs/1 mM dithiothreitol/1 U/ml RNAase Block (Stratagene)/50 mg/ml actinomycin D for 2 h at 37° C. The extended products were analyzed on denaturating 6% gel polyacrylamide gels. Sequence reactions on Flt-1 with the same primer were run in parallel for accurate determination of the extension termination site.

S1 mapping analysis was carried out as described Ausubel. F. M., Brent, R., Kingston, R. E., Moore, D. D., Seidman, J. G., Smith, J. A., and Struhl, K. (1987) *Current Protocols in Molecular Biology* (Wiley, New York), 4.6.1–4.6.13. Briefly, end labeled oligo-F was hybridized with pBKS3.0 and incubated with 4 units of Klenow fragment in the presence of 4 mM dNTPs for 30 min at 37° C. After heat inactivation, the extended product was digested with SmaI, separated on an alkaline agarose gel, and purified by phenol extraction and ethanol precipitation. The probe ($5\times10^4$ Cerenkov counts) was then hybridized to 50 mg of total RNA from HUVEC, human lung tissue (Clontech), or yeast tRNA in Hybridization buffer at 30° C. overnight. The reaction mixture was digested with 300 U of S1 nuclease in 280 mM NaCl/50 mM sodium acetate (pH 4.5)/4.5 mM $ZnSO_4$ for 60 min at 30° C. The protected products were analyzed on denaturating 6% polyacrylamide gels.

Example 2
Construction of Deletion Mutant Plasmids of the Flt-1 Promoter and Luciferase Fusion Genes Construction of p(-2.5k/+284)-luc Containing the 5'-flanking Region of Flt-1 and Luciferase-fusion Gene—The plasmid pMC-luc was generated by cloning annealed complementary oligonucleotides including restriction sites for SwaI, I-PpoI, PmeI, SmaI, AscI, NotI, XhoI, SrfI, SfiI, and HindIII
(5'-ATTTAAATCTCTCTTAAGGTAGCGTTTAAACCC GGGCGCGCCGCGGCCGCTCGAGCCCGGGCGGCC TCACTGGCCATTTAAATA-3' (SEQ ID NO:7) and
5'-AGCTTATTTAAATGGCCAGTGAGGCCGCCCGGG CTCGAGCGGCCGCGGCGCGCCCGGGTTTAAACG CTACCTTAAGAGAGATTTAAAT-3') (SEQ ID NO:8) into the SmaI and HindIII sites of a luciferase expression vector (pGL2-basic, Promega). A 3 kb NotI/XhoI fragment from pBKS3.0 which contains the 5I-flanking region, the first exon, and part of the first intron of Flt-1 was inserted into the NotI and XhoI sites of pMC-luc to generate p(-2.5k/+550)-luc. A 3 kb SacI/KpnI fragment from pBKS3.0 was inserted into the KpnI and SacI sites of pGL2-basic to generate p(+550/-2.5k)-luc which contains the 5'-flanking region oriented in the reverse direction. The plasmid p(-2.5k/+284)-luc, in which most of the first intron was deleted, was constructed by digesting p(-2.5k/+550)-luc with NcoI, XhoI and Mung-Bean nuclease followed by self-ligation.

Construction of 5'-deletion Mutant Plasmids—The plasmid p(-1.9k/+284)-luc was constructed by digesting p(-2.5k/+284)-luc with PstI followed by self-ligation. The plasmid p(-1195/+284)-luc was constructed by digesting p(-2.5k/+284)-luc with PstI, BstXI, treating with T4 DNA polymerase, and self-ligating. To generate a series of deletion mutants, the plasmid p(-2.5k/+284)-luc was treated with BstXI, T4 DNA polymerase, and PstI, and digested with exonuclease III from 5'-end followed by self-ligation using Erase-a-Base kit (Promega). Several 5'-deletion mutants were produced: p(-962/+284)-luc, p(-748/+284)-luc, p(-583/+284)-luc, p(-386/+284)-luc, p(-356/+284)-luc, (-333/+284)-luc, p(-239/+284)-luc, p(-219/+284)-luc, and p(+151/+286)-luc. To construct another deletion mutant, p(-2.5k/+284)-luc was digested with AatII and PstI, treated with T4 DNA polymerase, and then self-ligated to generate p(-75/+284)-luc.

Construction of Luciferase-fusion Plasmids Containing a 5'-flanking Region, Exon 1, and a Hybrid Intron—The plasmid p(-2.5k/+550)sp-luc which contains a hybrid intron composed of the 5' portion of the first intron of Flt-1 and the 3' portion of mouse immunoglobulin heavy chain gene (Bothwell, A. L. M., Paskind, M., Reth, M., Imanishi-Kari, T., Rajewsky, K., and Baltimore, D. (1981) *Cell* 24, 625–637) was constructed by cloning annealed complementary oligonucleotides corresponding to a mouse immunoglobulin heavy chain variable region
(5'-TCGAGGCTTGAGGTCTGGACATATACATGGGTG ACAATGACATCCACTTTGCCTTTCTCTCCACAGG TGTCCACTCCCAGGTCCAACTGCAG-3' (SEQ ID NO:9) and
5'-CTGCAGTTGGACCTGGGAGTGGACACCTGTGGA GAGAAAGGCAAAGTGGATGTCATTGTCACCCAT GTATATGTCCAGACCTCAAGCC-3') (SEQ ID NO:10) into the XhoI and SrfI sites of p(-2.5k/+550)-luc. The resulting plasmid p(-2.5k/+550)sp-luc was treated with XhoI, Klenow fragment, and NcoI and ligated with a 4 kb NcoI/EcoRI fragment from pBKS7.0 which contains the 5' portion of the first intron of Flt-1.

Construction of CREB/ATF Element-deleted Mutant Plasmids—The plasmid p(-962/+284)-luc was digested with AatII and treated with T4 DNA polymerase, resulting in pΔCRE(-962/+284)-luc. Four internal bases of CREB/ATF element (ACGT out of TGACGTCA) were deleted in pDCRE(-962/+284)-luc.

Example 3
Preparation of Transfected Cells and Enzyme Assays

For transfection analyses, the plasmids described in Example 2 were purified with Wizard Megaprep (Promega) followed by cesium chloride gradient ultracentrifugation. BAEC and NIH-3T3 cells were seeded onto 6-well plates or, for HFF, onto 100 mm dishes at a density adjusted so that they reached 40–60% confluence prior to transfection. For BAEC and NIH-3T3 cells, 5 mg DNA of test plasmid, 5 mg of pSV-CAT (pCAT-promoter, Promega), and 10 ml (5 ml for NIH-3T3 cells) of lipofectin (GibcoBRL) were incubated in 0.1 ml OptiMEM (GibcoBRL) for 20 min. Similarly, for HFF, 25 mg plasmid construct DNA and 5 mg DNA of PSV-CAT, and 50 ml of lipofectin were incubated in 0.4 ml of OptiMEM. The resulting transfection mixture was added to the medium and incubated for 6–10 h at 37° C. Then, the medium was replaced by complete medium for an additional 3 days. For the stimulation experiments, 10 mM forskolin and 0.5 mM 3-iso-butyryl-1-methyl-xanthine (IBMX) or 0.5 mM dibutyryl-cAMP and 0.5 mM IBMX were added directly to media 16–17 h prior to harvest. Cells were washed with ice-cold PBS twice, and lysed with 80 ml (6-well plate) or 400 ml (10 cm dish) of 100 mM potassium phosphate (pH 7.8)/0.5% Triton X-100. After removing the insoluble cell debris by centrifugation, each cell lysate was used to measure luciferase and CAT activities. The luciferase activity was measured with a Monolight 2010 luminometer in the presence of 1 mM DTT using Luciferase Assay Reagent (Promega). CAT activity was determined by the phase-extraction procedure using [$^3$H]chloramphenicol (Du Pont-New England Nuclear) and xylenes after endogenous deacetylating activity was destroyed by heating the lysates for 10 min at 65° C. (Seed, B. and Sheen, J. -Y. (1988) Gene(Amst.) 67, 271–277). The efficiency of transfections was normalized with activities of CAT assay.

Figure 6B:
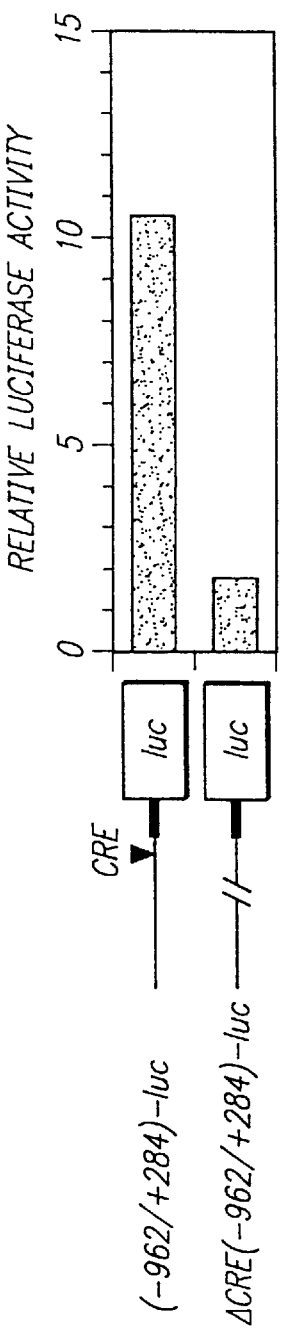

Results are shown in FIGS. 4 and 6A (5'-deletion mutants) and FIG. 6B (CREB/ATF deletion mutant). Deletion mutant p(-748/+284)-luc showed the highest activity. Transfection of the series of constructs deleted from -2.5 kb to +151 suggested the presence of at least two regions, 2500 to -1195 and -356 to -333, containing negative regulatory sequences, and two regions, -748 to -583 and -239 to -75, containing positively regulatory sequences. Deletion to +151 decreased luciferase activity to the level of the promoterless plasmid pMC-luc. Deletion of 4 internal bases in the CREB/ATF element of the flt-1 promoter (ACGT out of TGACGTCA) diminished relative luciferase activity in BAEC by 85% (FIG. 6B). However, it was not possible to detect any stimulation of luciferase activity in response to forskolin/IBMX and dibutyryl-cAMP/IBMX in BAEC transfected with either p(-962/+284)-luc or pDCRE(-962/+284)-luc (data not shown). Therefore, the CREB/ATF element of the Flt-1 promoter is important for basal transcription of Flt-1, but may not be important in the transcriptional activation in response to CAMP elevation.

The First Intron of flt-1 Negatively Regulated Transcription—Transfection of the p(-2.5k/+550)-luc construct, which contains 220 bp of the first intron of flt-1 (containing the 5' splice site but not the 3' splice site), resulted in no luciferase activity (FIG. 7). This may be due to the production of an undesirable protein instead of luciferase since the first intron contains an ATG at +286 which is up-stream of the initiation codon of the luciferase gene and may not be spliced out because of the lack of a 3' splice site. When a 3' splice site from a mouse immunoglobulin gene (10) was introduced down-stream of the first intron to generate a hybrid intron (p(-2.5k/550)sp-luc), luciferase activity was partially restored. The idea to make this construct was based on results obtained with a hybrid intron consisting of a 5' splice site from the first exon of the adenovirus tripartite leader and a 3' splice site from a mouse immunoglobulin gene on pMT2 expression vector (Kaufman, R. J., Davies, M. V., Pathak, V. K., and Hershey, J. W. B. (1989) Mol. Cell. Biol. 9, 946–958). These studies showed that the hybrid intron was completely spliced out when eukaryotic initiation factor 2 was expressed on pMT2 vector. Thus, it appears likely that the decrease of luciferase activity seen in p(-2.5k/550)sp-luc (FIG. 7) does not result from a deficiency in splicing. Therefore, it was concluded that the first intron of flt-1 negatively regulated the transcription.

Example 4

Preparation of Transfected Cells with the Flt-1 Promoter Using Viral Vectors and Enzyme Assays Construction of a recombinant adenovirus containing the Flt-1 promoter—luciferase fusion gene and enzyme assays—The plasmid p(-748/+284)-luc was digested with SalI, treated with T4 DNA polymerase, and digested with BamHI to generate a 3.7 kb fragment. The fragment was cloned into the SwaI site of pAdex1W adenovirus cosmid vector, Y. Nakamura et al., Cancer Research, 54, 5757–5760 (1994), to generate pAdexFLTP-luc. pAdexFLTP-luc and the EcoT22I-digested adenoviral DNA-TPC were co-transfected into 293 cells to prepare a replication-negative recombinant adenovirus AdexFLTP-luc (Kanegae, Y., Makimura, M., and Saito, I. (1994) Jpn. J. Med. Sci. Biol., 47, 157–166). A recombinant adenovirus AdexlCA-LacZ which contains a CAG promoter (modified chicken b-actin promoter with CMV-IE enhancer) (Niwa, H., Yamamura, K., and Miyazaki, J. (1991) Gene, 108, 193–200) and a b-galactosidase gene and AdexFLTP-luc were used to co-infect with various cell lines (HAEC, HPEC, HUVEC, BAEC, HMEC, AOSMC, NCI-H292, HFF, RASMC, and NIH-3T3). Briefly, AdexFLTP-luc (1.1× $10^5$ pfu/ml) and AdexCAlLacZ (8.4×$10^4$ pfu/ml) were incubated with cells in 0.5 ml of DMEM supplemented with 10% FBS in 24-well plates. Luciferase activity was measured as described above and β-galactosidase activity was measured with chlorophenol red β-D-galactopyranoside (Boehringer Mannheim Biochemica). The efficiencies of transfections were normalized with activities of b-galactosidase assays. Results are shown in FIG. 5 and demonstrate that the Flt-1 promoter region between positions -748 and +284 conferred endothelial-specific gene expression.

Although the foregoing invention has been described in some detail by way of illustration and example for the purposes of clarity and understanding, it will be obvious that certain changes and modifications may be practiced within the scope of the appended claims. All patents, patent applications and publications described herein are herewith incorporated by reference.

What is claimed is:

1. An assay for screening for a test compound that regulates the activity of a VEGF receptor promoter comprising:

(a) contacting one or more isolated host cells, wherein said host cells are transformed with an expression vector comprising an isolated nucleic acid molecule which comprises a VEGF receptor promoter region, wherein said promoter region is the promoter contained in SEQ ID NO: 1 and said promoter being operably linked to a reporter gene encoding a gene product, with a test medium containing said test compound under conditions which allow for expression of said reporter gene;

(b) measuring the expression of the reporter gene of (a) in the presence of said test medium;

(c) contacting one or more isolated host cells, wherein said host cells are transformed with an expression vector comprising an isolated nucleic acid molecule which comprises a VEGF receptor promoter region, said promoter region being contained in SEQ ID NO: 1 and said promoter being operably linked to a reporter gene encoding a gene product, with a control medium which does not contain said test compound but is otherwise identical to said test medium in (a), under conditions identical to those used in (a);

(d) measuring the expression of the reporter gene of (c) in the presence of said control medium; and (e) wherein the difference in expression between (b) and (d) indicates the test compound regulates the activity of the VEGF receptor promoter.

2. The method of claim 1, wherein the reporter gene is the luciferase gene.

3. The method of claim 1, wherein the reporter gene is the chloramphenicol acetyl tansferase gene.

4. The method of claim 1, wherein the host cell is a mammalian cell.

5. The method of claim 1, wherein the host cell is an endothelial cell.

6. An assay for measuring the ability of a test compound to modulate VEGF receptor transcription comprising:

(a) contacting one or more isolated host cells, wherein said host cells are transformed with an expression vector comprising an isolated nucleic acid molecule which comprises a VEGF receptor promoter region, said promoter region being contained in SEQ ID NO: 1 and said promoter being operably linked to a reporter gene encoding a gene product, with an inducer of VEGF receptor promoter activity under conditions which allow for expression of said reporter gene;

(b) measuring the expression of said reporter gene in the absence of the test compound;

(c) exposing the host cells to the test compound either prior to, simultaneously with, or after contacting, the host cells with the inducer;

(d) measuring the expression of said reporter gene in the presence of the test compound; and (e) wherein the difference in expression between (b) and (d) indicates the test compound modulates VEGF receptor transcription.

7. The method of claim 6, wherein the reporter gene is the luciferase gene.

8. The method of claim 6, wherein the reporter gene is the chloramphenicol acetyl transferase gene.

9. The method of claim 6, wherein the host cell is a mammalian cell.

10. The method of claim 9, wherein the host cell is an endothelial cell.

11. A method of determining whether a test compound is an antagonist or agonist of the VEGF/VEGF receptor regulatory system, the method compri sing:

(a) incubating an isolated host cell transformed with an expression vector comprising an isolated nucleic acid molecule which comprises a VEGF receptor promoter region, said promoter region contained in SEQ ID NO: 1 and said promoter operably linked to a gene encoding a gene product, wherein said gene product is a VEGF receptor with a test medium containing said test compound and a labeled VEGF under conditions which allow for binding of the labeled VEGF to the host cell;

(b) measuring the binding of labeled VEGF to said cell in the presence of the test compound;

(c) incubating an isolated host cell, wherein said host cell is transformed with an expression vector comprising an isolated nucleic acid molecule which comprises a VEGF receptor promoter region, said promoter region being contained in SEQ ID NO: 1 and said promoter being operably linked to a gene encoding a gene product, wherein said gene product is a VEGF receptor, with a control medium which does not contain said test compound but is otherwise identical to the test medium in (a) and a labeled VEGF, under conditions identical to (a);

(d) measuring the binding of labeled VEGF to said cell in the presence of the control medium; and (e) comparing the binding of labeled VEGF in (b) to the binding of labeled VEGF in (d) wherein the difference between the binding in (b) and the binding in (d) indicates that the test compound is an agonist or antagon the VEGF receptor.

12. The method of claim 11, wherein the host cell is a mammalian cell.

13. The method of claim 12, wherein the host cell is an endothelial cell.

* * * * *

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
        (A) LENGTH: 1745 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..1195
        (D) OTHER INFORMATION: /note= "Nucleotides numbered 1
            through 1195 correspond to -1195 through -1 from
            Figure 2."

(xi) SEQUENCE DESCRIPTION: SEQ ID NO: 1:

```
GTGGCAACTT TGGGTTACCC AACCTTCCTA GGCGGGAGG  TAGTCCAGTC CTTCAGGAAG     60
AGTCTCTGGC TCCGTTCAAG AGCCATCACA GTCCCTTGTA TTACATCCCT CTGACGGGTT    120
CCAATAGGAC TATTTTTCAA ATCTGCGGTA TTTACAGAGA CAAGACTGGG CTGCTCCGTG    180
CAGCCAGGAC GACTTCAGCC TTTGAGGTAA TGGAGACATA ATTGAGGAAC AACGTGGAAT    240
TAGTGTCATA GCAAATGATC TAGGGCCTCA AGTTAATTTC AGCCGGTTGT GGTCAGAGTC    300
ACTCATCTTG AGTAGCAAGC TGCCACCAGA AAGATTTCTT TTTCGAGCAT TTAGGGAATA    360
AAGTTCAAGT GCCCTGCGCT TCCAAGTTGC AGGAGCAGTT TCACGCCTCA GCTTTTTAAA    420
GGTATCATAA TGTTATTCCT TGTTTTGCTT CTAGGAAGCA GAAGACTGAG GAAATGACTT    480
GGGCGGGTGC ATCAATGCGG CCGAAAAAGA CACGGACACG CTCCCCTGGG ACCTGAGCTG    540
GTTCGCAGTC TTCCCAAAGG TGCCAAGCAA GCGTCAGTTC CCCTCAGGCG CTCCAGGTTC    600
AGTGCCTTGT GCCGAGGGTC TCCGGTGCCT TCCTAGACTT CTCGGGACAG TCTGAAGGGG    660
TCAGGAGCGG CGGGACAGCG CGGGAAGAGC AGGCAAGGGG AGACAGCCGG ACTGCGCCTC    720
AGTCCTCCGT GCCAAGAACA CCGTCGCGGA GGCGCGGCCA GCTTCCCTTG GATCGGACTT    780
TCCGCCCCTA GGGCCAGGCG GCGGAGCTTC AGCCTTGTCC CTTCCCCAGT TTCGGGCGGC    840
CCCCAGAGCT GAGTAAGCCG GGTGGAGGGA GTCTGCAAGG ATTTCCTGAG CGCGATGGGC    900
AGGAGGAGGG GCAAGGGCAA GAGGGCGCGG AGCAAAGACC CTGAACCTGC CGGGGCCGCG    960
CTCCCGGGCC CGCGTCGCCA GCACCTCCCC ACGCGCGCTC GGCCCCGGGC CACCCGCCCT   1020
CGTCGGCCCC CGCCCCTCTC CGTAGCCGCA GGGAAGCGAG CCTGGGAGGA AGAAGAGGGT   1080
AGGTGGGGAG GCGGATGAGG GGTGGGGGAC CCCTTGACGT CACCAGAAGG AGGTGCCGGG   1140
GTAGGAAGTG GGCTGGGGAA AGGTTATAAA TCGCCCCCGC CCTCGGCTGC TCTTCATCGA   1200
GGTCCGCGGG AGGCTCGGAG CGCGCCAGGC GGACACTCCT CTCGGCTCCT CCCCGGCAGC   1260
GGCGGCGGCT CGGAGCGGGC TCCGGGGCTC GGGTGCAGCG GCCAGCGGGC GCCTGGCGGC   1320
GAGGATTACC CGGGGAAGTG GTTGTCTCCT GGCTGGAGCC GCGAGACGGG CGCTCAGGGC   1380
GCGGGGCCGG CGGCGGCGAA CGAGAGGACG GACTCTGGCG GCCGGGTCTT TGGCCGCGGG   1440
GAGCGCGGGC ACCGGGCGAG CAGGCCGCGT CGCGCTCACC ATGGTCAGCT ACTGGGACAC   1500
CGGGGTCCTG CTGTGCGCGC TGCTCAGCTG TCTGCTTCTC ACAGGTGAGG CGCGGCTGGG   1560
GGCCGGGGCC TGAGGCGGGC TGCGATGGGC CGGCCGGAGG GCAGAGCCTC CGAGGCCAGG   1620
GCGGGGTGCA CGCGGGGAGA CGAGGCTGTA GCCCGGAGAA GCTGGCTACG GCGAGAACCT   1680
GGGACACTAG TTGCAGCGGG CACGCTTGGG GCCGCTGCGC CCTTTCTCCG AGGGAGCGCC   1740
TCGAG                                                              1745
```

(2) INFORMATION FOR SEQ ID NO: 2:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 2:

```
AGGGGCTCCG TTGCCAGGGT TCTGT                                   25
```

(2) INFORMATION FOR SEQ ID NO: 3:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 3:

```
GGACACTCCT CTCGGCTCCT CCCCGGCAGC GGCGGCGGCT CGG               43
```

(2) INFORMATION FOR SEQ ID NO: 4:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 4:

```
CGCTGGCCGC TGCACCCGAG CCCCGGAGCC CGCTCCGAGC CGCCGC            46
```

(2) INFORMATION FOR SEQ ID NO: 5:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 5:

```
GGTCTTTGCC TGAAATGGTG AGTAAGGAAA GCGAAAGGCT GAGCATAACT        50
```

(2) INFORMATION FOR SEQ ID NO: 6:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 6:

```
CAGAATTGTT TGCCATTTCT TCCACAGGCA GATTTAGTTA TGCTCAGCCT        50
```

(2) INFORMATION FOR SEQ ID NO: 7:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 7:

```
ATTTAAATCT CTCTTAAGGT AGCGTTTAAA CCCGGGCGCG CCGCGGCCGC TCGAGCCCGG          60

GCGGCCTCAC TGGCCATTTA AATA                                                84
```

(2) INFORMATION FOR SEQ ID NO: 8:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 8:

```
AGCTTATTTA AATGGCCAGT GAGGCCGCCC GGGCTCGAGC GGCCGCGGCG CGCCCGGGTT          60

TAAACGCTAC CTTAAGAGAG ATTTAAAT                                            88
```

(2) INFORMATION FOR SEQ ID NO: 9:

(i) SEQUENCE CHARACTERISTICS:
        (A) LENGTH: 92 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 9:

```
TCGAGGCTTG AGGTCTGGAC ATATACATGG GTGACAATGA CATCCACTTT GCCTTTCTCT          60

CCACAGGTGT CCACTCCCAG GTCCAACTGC AG                                       92
```

(2) INFORMATION FOR SEQ ID NO: 10:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 10:

```
CTGCAGTTGG ACCTGGGAGT GGACACCTGT GGAGAGAAAG GCAAAGTGGA TGTCATTGTC          60

ACCCATGTAT ATGTCCAGAC CTCAAGCC                                            88
```